(12) United States Patent
Snyder et al.

(10) Patent No.: US 11,485,969 B2
(45) Date of Patent: Nov. 1, 2022

(54) COLLECTOR DEVICE OF ENVIRONMENTAL EXPOSURE FOR BIOTIC AND ABIOTIC AGENTS

(71) Applicant: The Board of Trustees of the Leland Stanford Junior University, Stanford, CA (US)

(72) Inventors: Michael Snyder, Stanford, CA (US); Jingga Inlora, Mountain View, CA (US); Chao Jiang, Mountain View, CA (US); Xiyan Li, Mountain View, CA (US); Ting Wang, Cupertino, CA (US); Xin Wang, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 165 days.

(21) Appl. No.: 16/606,801

(22) PCT Filed: Apr. 20, 2018

(86) PCT No.: PCT/US2018/028538
§ 371 (c)(1),
(2) Date: Oct. 21, 2019

(87) PCT Pub. No.: WO2018/195401
PCT Pub. Date: Oct. 25, 2018

(65) Prior Publication Data
US 2020/0377927 A1    Dec. 3, 2020

Related U.S. Application Data

(60) Provisional application No. 62/488,256, filed on Apr. 21, 2017, provisional application No. 62/617,471, (Continued)

(51) Int. Cl.
  *C12Q 1/68* (2018.01)
  *C12N 15/10* (2006.01)
  (Continued)

(52) U.S. Cl.
  CPC ..... *C12N 15/1089* (2013.01); *C12N 15/1017* (2013.01); *C12N 15/1093* (2013.01);
  (Continued)

(58) Field of Classification Search
  CPC ................................................. C12Q 1/68
  (Continued)

(56) References Cited

U.S. PATENT DOCUMENTS

2017/0114378 A1* 4/2017 Wochner ............... C12M 21/18

* cited by examiner

Primary Examiner — Aaron A Priest
(74) Attorney, Agent, or Firm — Lumen Patent Firm

(57) ABSTRACT

A collector device of environmental exposure is provided. This device may be used to collect and, after technical upgrade, monitor environmental exposure in personal and stationary settings. By coupling with advanced genomic analysis and chemical analysis technologies, the device and its accompanying methodology are capable of detecting environmental agents of diverse nature, many of which could pose health risks if going unaware of or uncontrolled. This type of information provides much needed clues to reconstruct and pinpoint the course of disease etiology at both personal and epidemic scales. By combining personal exposome and personal omics analyses, we can recapitulate with the intention to then prescribe treatment plans with unprecedented precision.

5 Claims, 18 Drawing Sheets

Related U.S. Application Data filed on Jan. 15, 2018, provisional application No. 62/488,119, filed on Apr. 21, 2017.

(51) Int. Cl.
| | |
|---|---|
| *G16B 20/00* | (2019.01) |
| *G16B 30/20* | (2019.01) |
| *G01N 30/00* | (2006.01) |
| *G01N 33/00* | (2006.01) |
| *C12Q 1/6806* | (2018.01) |
| *C12Q 1/6869* | (2018.01) |
| *G16B 40/20* | (2019.01) |

(52) U.S. Cl.
CPC ......... *C12Q 1/6806* (2013.01); *C12Q 1/6869* (2013.01); *G01N 30/00* (2013.01); *G01N 33/0004* (2013.01); *G16B 20/00* (2019.02); *G16B 30/20* (2019.02); *G16B 40/20* (2019.02); *G01N 2030/009* (2013.01)

(58) Field of Classification Search
USPC ........................................................ 435/6.1
See application file for complete search history.

Collection

1. Device is turned on and actively collecting samples via air pump

Sample processing and analysis

| | |
|---|---|
| 2a. Filter is removed from device for biotic materials processing | 2b. Resin-containing cartridge is removed from device for abiotic materials processing |
| 3a. DNA and RNA extraction from the filter | 3b. Compound extraction using methanol |
| 4a. DNA and RNA amplification and library prep | 4b. LC/MS analysis using UPLC-coupled exactive orbitrap mass spectrometer |
| 5a. Sequencing on Next Generation Sequencing (NGS) platform | 5b. Raw LC/MS files are analyzed using PAVA, XCMS and SIMCA softwares |
| 6a. Sequence analysis and identification of biotic agents via LCA | |

Results and interpretation

Reporting of biotic and abiotic materials that are present in the air

FIG. 1

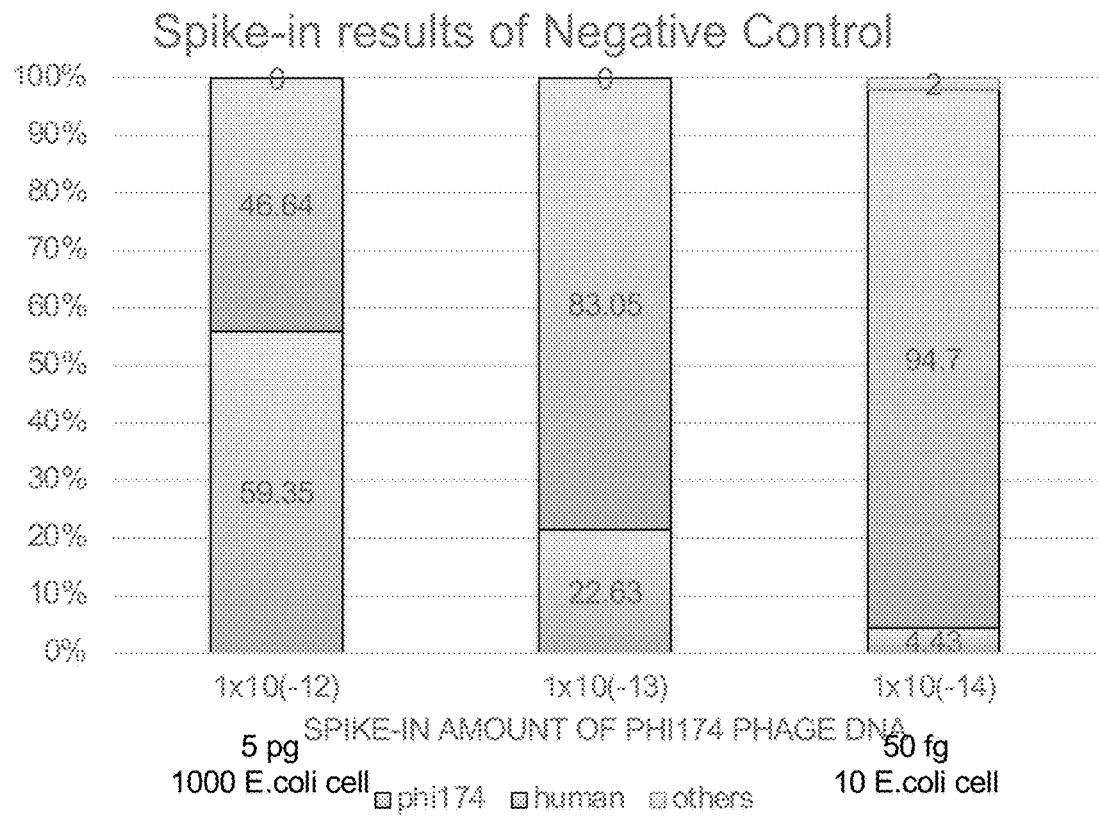
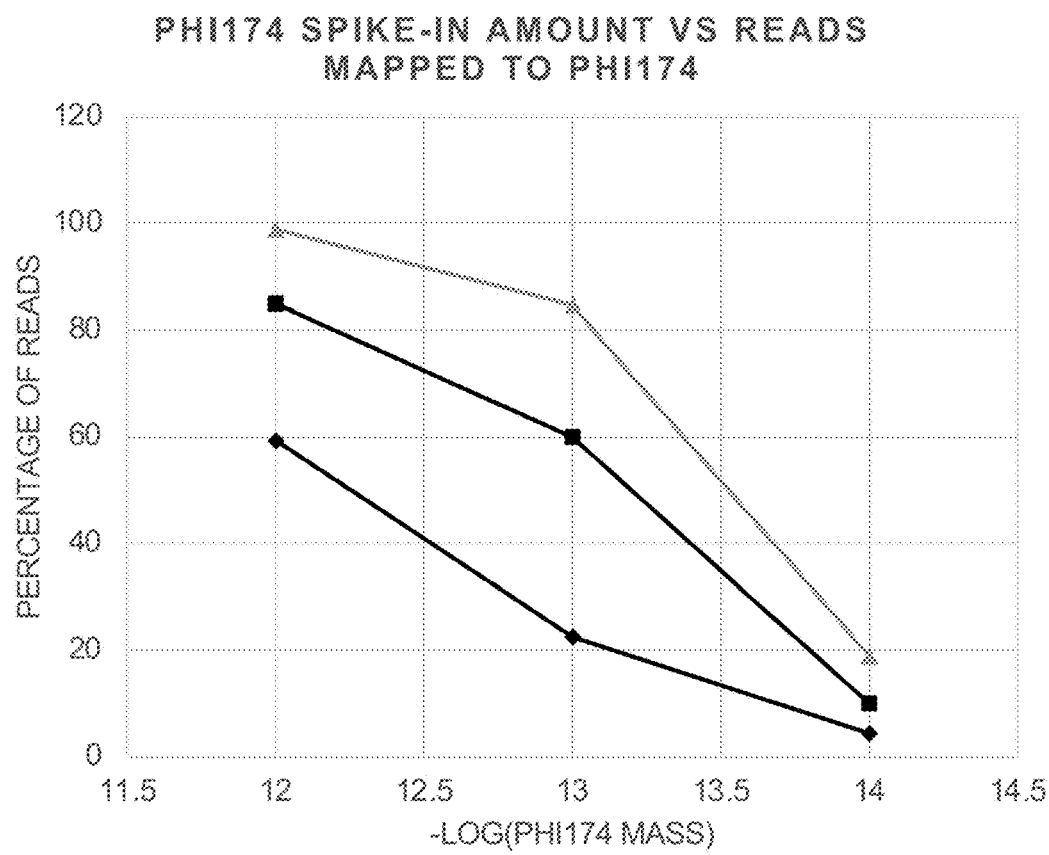
FIG. 3B

| Copies | Name | detection |
|---|---|---|
| 200 | Human parainfluenza virus 3 | YES |
| 200 | Rhinovirus 1A | YES |
| 400 | Human metapneumovirus | YES |
| 400 | Betacoronavirus 1 (coronavirus OC43) | YES |
| 400 | Enterovirus B | YES |
| 1000 | Human respiratory syncytial virus | YES |
| 1000 | Coronavirus 229E (alphacoronavirus) | YES |
| 1000 | Human parainfluenza virus 2 | YES |
| 1000 | Influenza B virus | YES |
| 1400 | Influenza A virus | YES |
| 10000 | Human immunodeficiency virus 1 | YES |
| 10000 | Cowpea mosaic virus | YES |

FIG. 8

COLLECTOR DEVICE OF ENVIRONMENTAL EXPOSURE FOR BIOTIC AND ABIOTIC AGENTS

CROSS-REFERENCE TO RELATED APPLICATIONS

This application is a 371 of PCT application PCT/US2018/028538 filed Apr. 20, 2018. PCT application PCT/US2018/028538 claims the benefit of U.S. Provisional Applications 62/488,256 filed Apr. 21, 2017, 62/617,471 filed Jan. 15, 2018, and 62/488,119 filed Apr. 21, 2017.

STATEMENT OF GOVERNMENT SPONSORED SUPPORT

This invention was made with Government support under contract DK102556 awarded by the National Institutes of Health. The Government has certain rights in the invention.

FIELD OF THE INVENTION

This invention relates to collector devices of environmental exposure for biotic and abiotic agents.

BACKGROUND OF THE INVENTION

Human health can be viewed as the interactive outcome between inherited traits and exposed environmental risks. From womb to tomb, the human body is exposed to a plethora of environmental agents from within and outside, which is termed "exposome" and contains diverse biotic agents (bacteria, viruses, fungi, pollen, etc.) and abiotic chemicals (smog dust, pesticides, chemical waste). Upon contraction, the exposome agents can greatly affect human health. Therefore, by complementing personal omic analysis, exposome analysis helps provide a holistic view of human health and disease states.

To make an effective individualized treatment, as the current paradigm of personalized medicine or precision medicine has envisioned, we must first know what risks an individual are exposed to as well as his genetic predispositions. In contrast to the rich information and convenient access of the genome analyses, understanding of the exposome is still very limited, which cripples our current effort in providing effective individualized treatment. The present invention intends at least some of the shortcomings in the art towards a collector device of environmental exposure.

SUMMARY OF THE INVENTION

In this invention, we describe a collector device of environmental exposure. This device may be used to collect and, after technical upgrade, monitor environmental exposure in personal and stationary settings. By coupling with advanced genomic analysis as described herein (see APPENDIX infra) and chemical analysis technologies, we are able to demonstrate that the device and its accompanying methodology are capable of detecting environmental agents of diverse nature, many of which could pose health risks if going unaware of or uncontrolled. This type of information provides much needed clues to reconstruct and pinpoint the course of disease etiology at both personal and epidemic scales. By combining personal exposome and personal omics analyses, we can recapitulate with the intention to then prescribe treatment plans with unprecedented precision.

The genomic analysis platform has become an integral part in developing next generation medicine and healthcare. The market of human genomics analysis has reached 12.5 billion dollars in 2015 and is expected to grow at 10% annually to 20 billion dollars by 2020. However, the exposome analysis platform has not showed up yet. Our innovation will not only help the overall development of precision medicine, but also to prevent and control diseases.

In one embodiment, the invention provides a collector device of environmental exposure for biotic and abiotic agents. The device distinguishes a housing with a front-end for air inlet and a rear-end for air outlet. An air pump is situated in between the air inlet and the air outlet. The air pump is controlled to provide a constant air flow for air intake at the air inlet.

A membrane filter (e.g. a polyethersulfone (PES) or a regenerated cellulose membrane filter) is situated in between the air flow from the front-end for air inlet and the air pump. The membrane filter has pores with a pore size ranging from 0.1 to 5 µm to collect particulate matters from the constant air flow. In another example, the pore size ranges from 0.22 to 0.8 µm. A biotic analyzing unit analyzes biotic samples from the collected particulate matters collected at the membrane filter.

A compound sorbent cartridge is situated in between the air flow from the air pump and the rear-end for air outlet. The compound sorbent cartridge (e.g. made out of zeolite, graphene, or a combination thereof) has compound adsorption resin beads and pores ranging from 0.1 to 10 nm and a mesh size ranging from 45-60. An abiotic analyzing unit for analyzing abiotic samples from the collected particulate matters collected at the compound sorbent cartridge.

BRIEF DESCRIPTION OF THE DRAWINGS

FIG. 1 shows according to an exemplary embodiment of the invention an overall flowchart of detection of air biotic and abiotic particulates.

FIGS. 3A-C show according to an exemplary embodiment of the invention spike-in Phi174 provides a direct method to evaluate the original amount of sample in DNA (FIGS. 3A-B) and RNA (FIG. 3C).

FIG. 8 shows according to an exemplary embodiment of the invention that the pipeline has a sensitivity down to $10^2$ copies of individual viral species in a mixture of various RNA viruses and bacterial and yeast organisms. (the size of viral genome is 1/1000 E. coli cell).

DETAILED DESCRIPTION

A large portion of our daily environmental exposure comes from breathing and to fomites. An adult breathes in 11,000 liters of air per day, which means our lungs pump air at a rate of 7.6 liters per minute. At the current levels of environmental pollutants monitored by the EPA, an average person breathes in the following exposome substances every day:
1. 132 micrograms of PM2.5 dust that could be lodged in the lungs. This type of dust particulate matter include most bacteria and viruses, has a diameter of 2.5 micrometers or below, and can freely access our lungs through respiration.
2. 550 micrograms of PM10 dust. This type of dust include pollen and mold, and can access our upper respiratory airways.
3. Previously unmeasured amount of air-dissolved compounds, such as pesticide and repellent.

The Device

By design, the device is able to simultaneously capture all three types listed above. This collector device has the following features:
1. Active sampling. A constant air flow at 0.5 liter per minute, or one tenth of typical respiration rate, is maintained by a micro-sized pump ensures unbiased monitoring on the temporal scale.
2. Comprehensive sampling spectrum. Our device is capable of collecting both particulate matters and solvent compounds, which ensures unbiased monitoring on the analytical scale.
3. Flexible application settings. Our device is matchbox-sized, so it can be used as a wearable device for personal monitoring, or as a stationed device for public/group monitoring.
4. Integrated data handling and sample analysis. Our device is equipped with Bluetooth technology, and can communicate with other portable devices for convenient metadata reporting and analysis.

Figure 9:
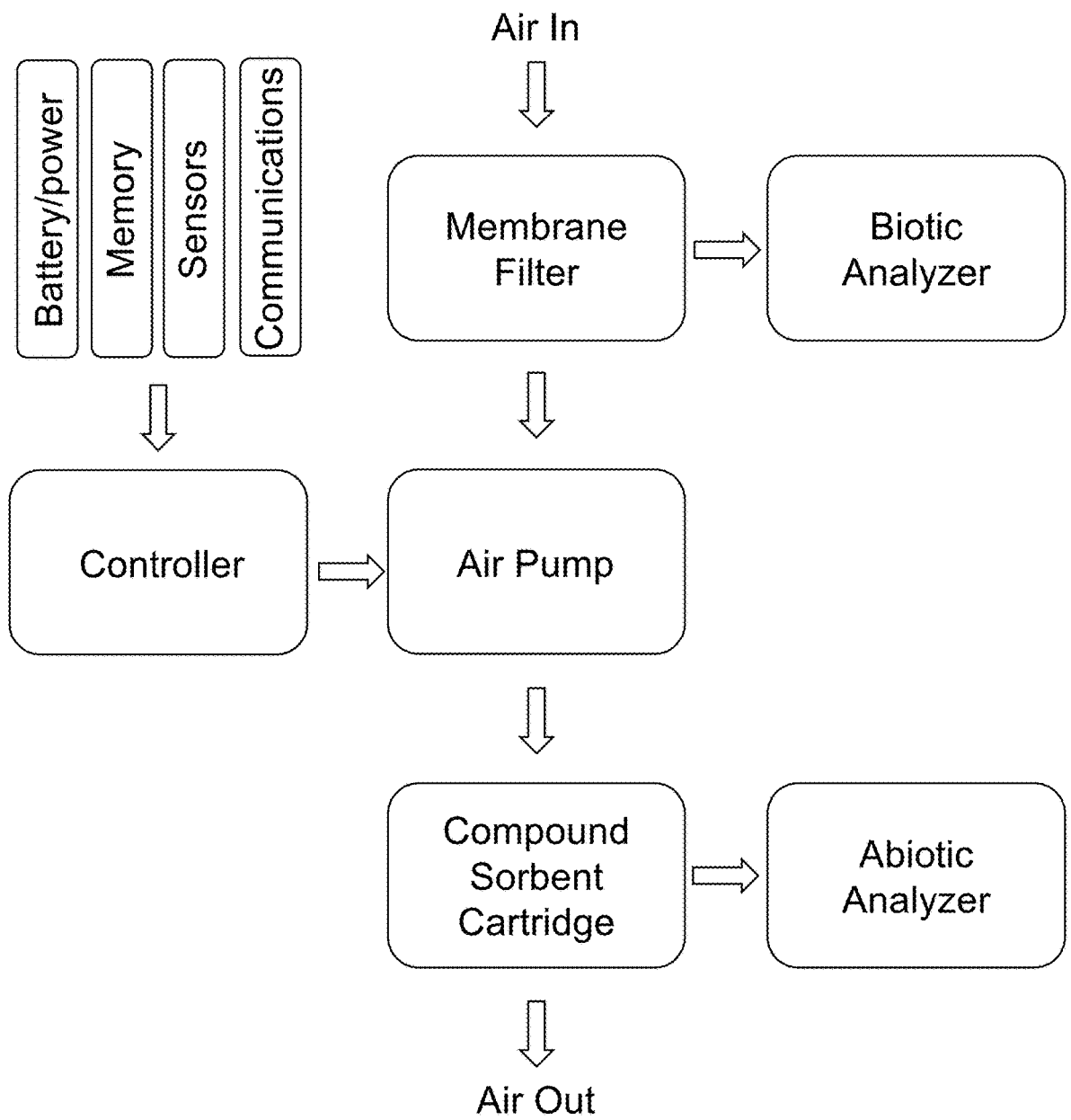
FIG. 9 shows according to an exemplary embodiment of the invention the collector device of environmental exposure for biotic and abiotic agents.

The portable device has three major parts (FIG. 9):
1. A rechargeable battery powers a micro air pump to main active air flow at a desired and adjustable rate. Under current estimation, the 2000 mA battery will last 12 hours or longer.
2. A printed circuit board (PCB, diagram design submitted) maintains the constant air flow from the pump through a voltage controller. The PCB also hosts other electronic sensors and modules, such as GPS, temperature sensor, humidity sensor, nephelometer, Bluetooth communication module, memory module as storage real-time data.
3. Two collecting units: the front unit is a membrane filter with defined pore sizes to collect the particulate matters from the constant air flow, the collected substance will be used for analysis of biological agents and also accommodate heavy metal analysis; the rear-end unit is a cartridge filled with molecule adsorbents to capture the compounds from the air, the captured compound will be analyzed by LC-MS as described in another section.

Size: the overall size of the portable device can be varied for its application. Notably, it may be the size of a dictionary for a stationary application, or it may be the size of a match box for wearable application.

Shape: the design the device can adopt a stylish flavor of artistic flavor. Both square and cylinder shape have been designed and will be tailored to the market taste once arriving at the stage.

The major components for this device are described below.

Exterior Shell

The exterior shell (FIG. 10) is designed in autoCAD and 3-D printed with plastic materials of high durability and light weight. The built-in inlet mesh serves as the first barrier to block debris of large size and protect the air way.

Air Pump

Figure 10:
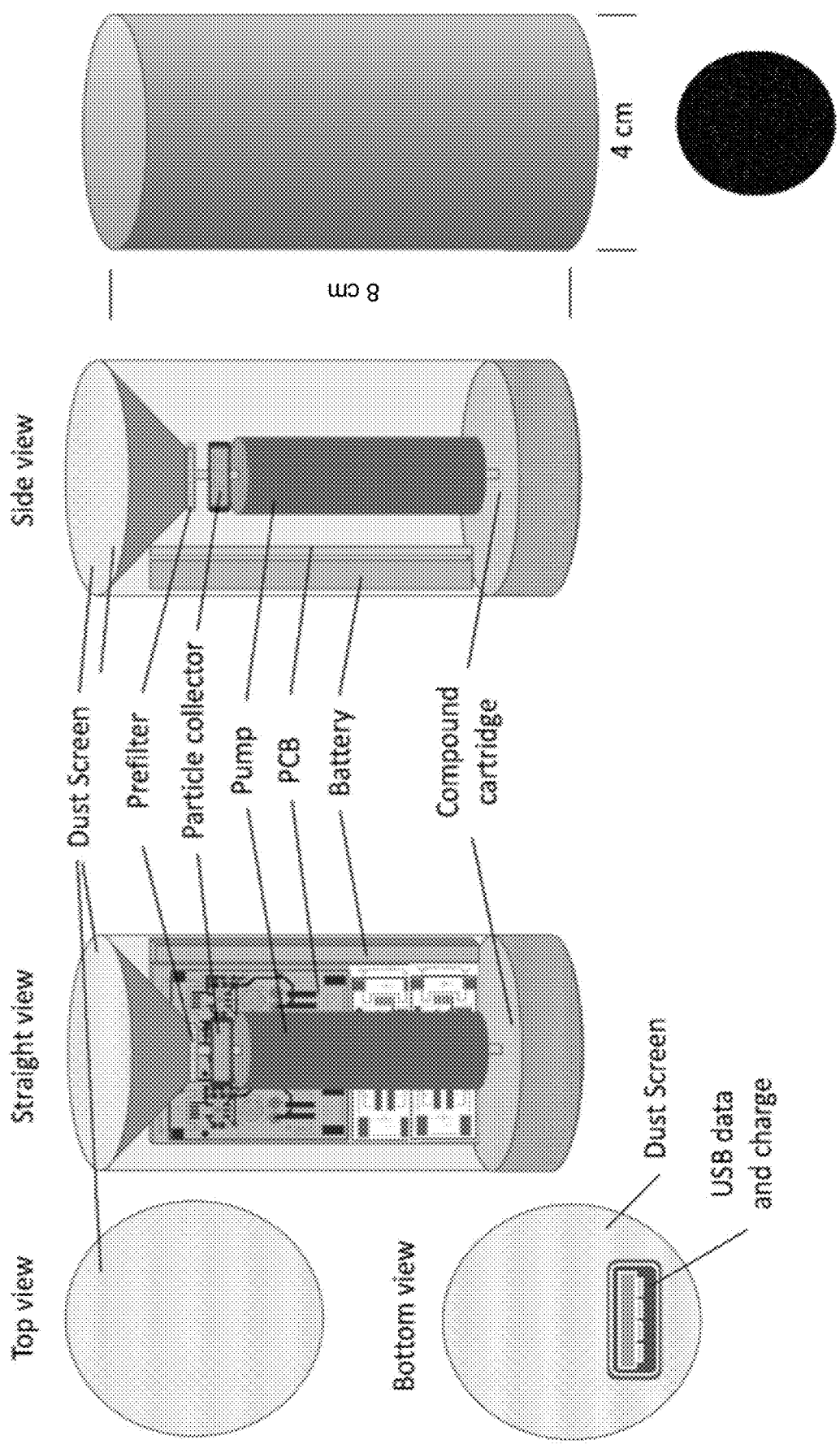
FIG. 10 shows according to an exemplary embodiment of the invention a design of the exposome collector device.

Air pump is the heart of the device and driving force provider for the active air flow. A variety of air pumps can be used for superior performance in maintaining constant air flow and energy consumption. An exemplary design uses a Germany-manufactured micro pump that is able to operate on a rechargeable lithium-ion battery cells and pump air at 0.5 liters/min for weeks without failure (FIG. 10).

Controlling Board

Figure 2:
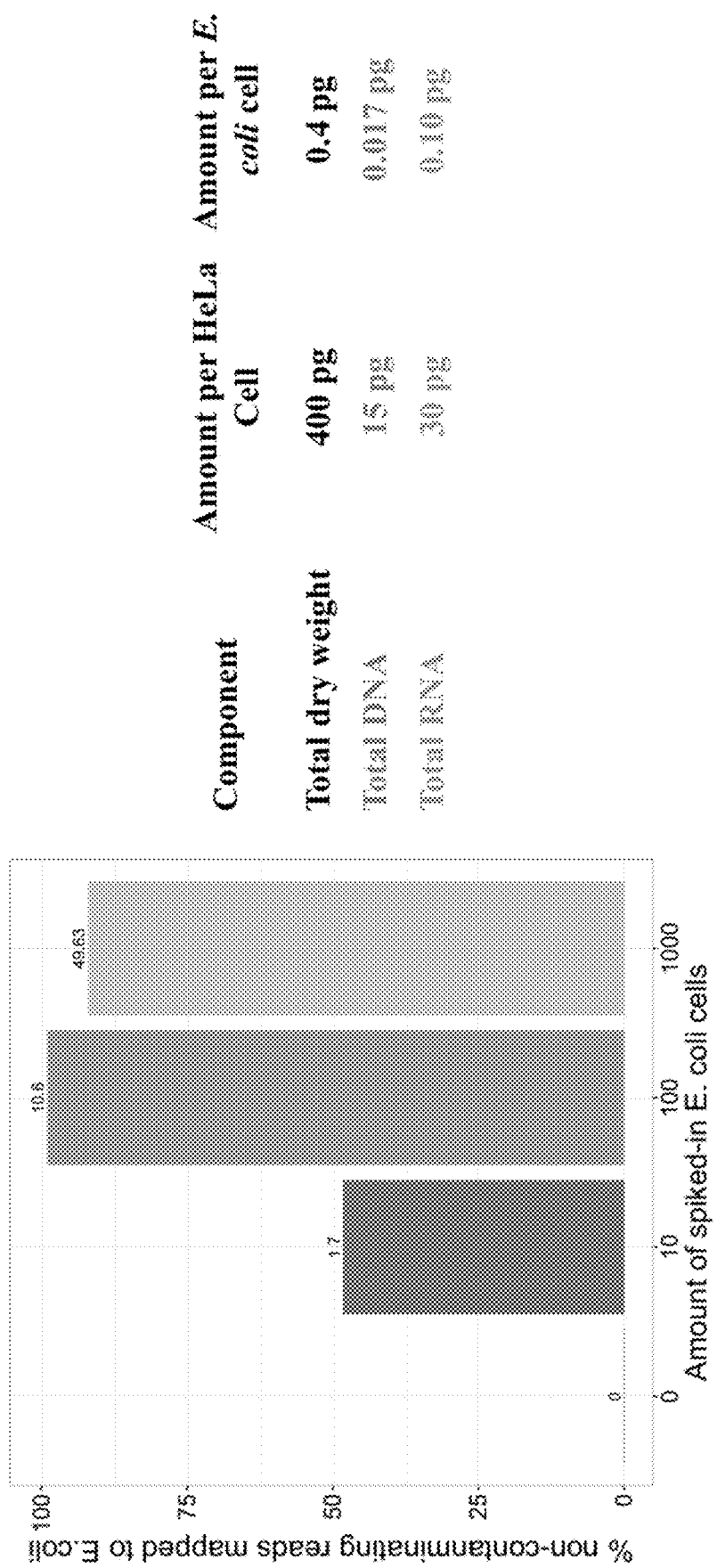
FIG. 2 shows according to an exemplary embodiment of the invention that the experimental pipeline can extract sufficient information from down to 10 (or even less) bacterial cells. Left, different amount of E. coli cells were spiked in before extraction and their numbers are evaluated by plating them on LB plates and counting. Right, the approximate amount of DNA and RNA from a typical E. coli cell as compared to a typical mammalian cell (HeLa cell).

The controlling microchip board in current design is slightly larger than a quarter coin (FIG. 2). Its main purpose is to control the air pump, to host a variety of mobile function chips (such as Bluetooth transmission, GPS location, temperature, humidity, particulate matter measurement, etc.), and to store and transmit real-time data for retrospective personal exposure reconstruction. We have the printed circuit board (PCB) prototype already manufactured.

Air Filter

Figure 11:
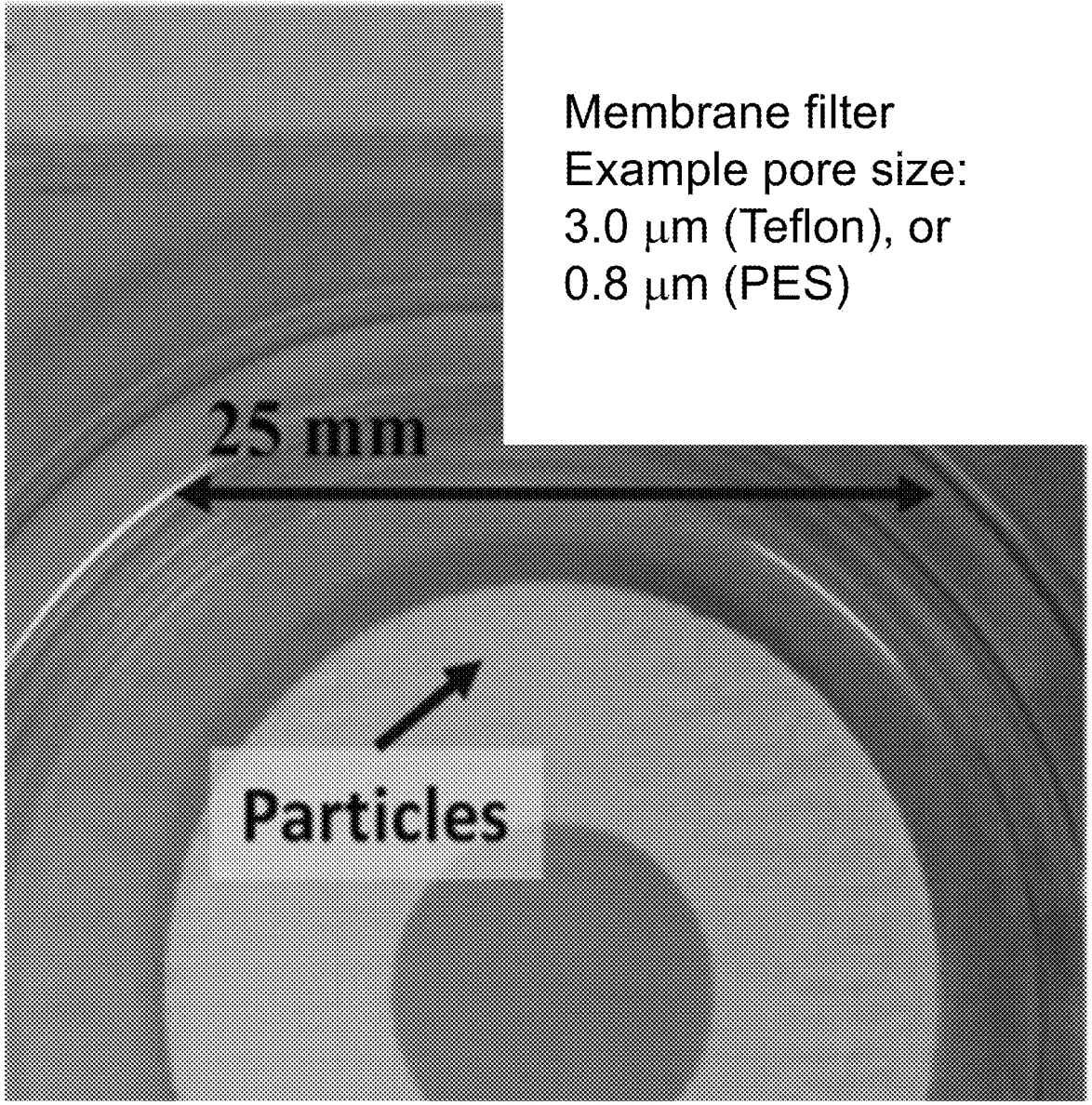
FIG. 11 shows according to an exemplary embodiment of the invention an air filter with actual collection of particulate matters at the center (darker region).

One or several layers of air filter are placed near the inlet to collect particulate matters (PM) from personal exposure. The filter is made of durable Teflon or polyethersulfone material and has pore sizes of 3.0 or 0.8 micrometers (FIG. 11). These two different formats are interchangeable with no noticeable difference in performance.

Compound Sorbent Cartridge

Figure 12:
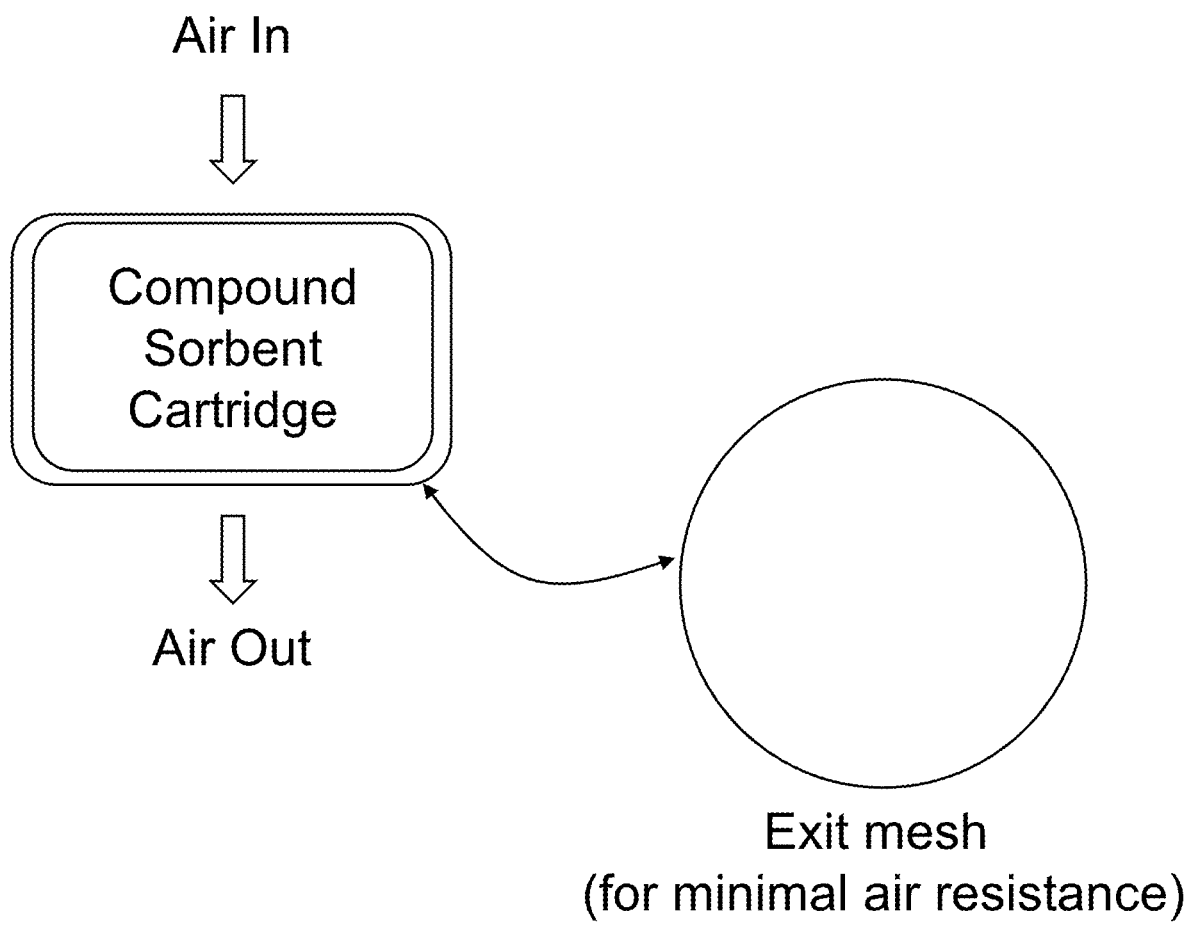
FIG. 12 shows according to an exemplary embodiment of the invention a Compound absorption (sorbent) cartridge. In one example, the sorbent materials were Sigma-Aldrich catalog #: 20304. Particle size: 45-60 mesh. Pore size: 13 Å pore diameter. Density: ~0.65 g/mL (free fall density). This resin is mainly used to in gas chromatography and remove impurity from gas/petroleum.

A cartridge housing compound adsorption resin beads is placed near the air outlet end in the device. The resin in use is a molecular sieve with 1.3 nanometer pore sizes and 45/60 mesh particle sizes, a type of material that is used in the petroleum industry to remove impurity compounds from oil product. (FIG. 12).

Collecting and Analyzing Biotic Samples

Biotic samples in exposure comprise of viruses, bacteria, fungi, pollen, and tiny particles of diverse nature due to incidental contact. These particulates range from sub-micrometer to tens of micrometers and are mainly collected on the air filter and analyzed by the platform as described herein in APPENDIX infra.

Collecting and Analyzing Abiotic Samples

Analysis of abiotic samples are performed in two ways:
1. the measurement of PM by size, just as the EPA standards for PM2.5 and PM10; Our on-board micro nephelometer sensor can detect the PM density in real time.
2. the analysis of air-borne chemicals, which are largely not monitored by the EPA at personal level but may pose various potential health risks. Our compound absorption cartridge is designed to collect these compounds.

We have developed a stream pipeline to extract compounds from the resin beads and analyze by liquid chromatography-coupled mass spectrometry. This assay was able to detect volatile flavonoid citrus compounds from orange peel, and unalarmed pesticide/repellant from real settings (not shown).

Applications

The device can be used for the following scenario:
1. a wearable device for constant monitoring of personal exposure. A patient with asthma or allergy symptoms wants to know what triggered the disease. By wearing our device for 1-2 weeks and analyzing his personal exposure by corroborating with the severity of his symptoms, the doctor will be able to find out the culprit agents and advise the patient against these agents in real life. Furthermore, the patient also has the chance to wear our device of an upgraded version to monitor his own allergens in real time and stay alert.
2. a stationed device for constant monitoring of public health. Appropriate measure for occupational safety and health is the mandatory obligation for US employers. It is known that occupational exposure increases cancer and heart disease ricks. According to the CDC, occupational illnesses cost 14 billion dollars in the United States every year, of which cancer and heart disease cost 9 billion dollars and cause 12,000-26,000 deaths and 6,000-18,000 deaths, respectively. A versatile monitoring system, such as our device and accompanying analyses for both biotic and abiotic exposures, will be instrumental to accurate and timely monitoring of health damaging agents in workspace.
3. a stationed device in a surveillance system for epidemic diseases. Public space, such as airports, subway and train stations, abound in both people and pathogens, which makes them hotbeds for outbreak of air-borne contagious diseases, such as the bird and pig flus in recent years. Our device may be deployed in such places and monitored periodically for the biotic agents. The results may be used to identify new strains and predict epidemic trend of public health-threating diseases such as flu, and also to provide the footprint retrospectively on a disease outbreak, such as the genomic surveillance of Ebola incidence in 2016.

Variations

The device and analysis could evolve into two major formats:
1. an exposure collector. This format has both personal and stationed application for untargeted exposure analysis, which has the widest spectrum anyone could provide, to our knowledge. By coupling the device with our proprietary analysis pipeline, our detection capability will be as good as the boundary of human knowledge allows.
2. a real time monitor. This format mainly targets a handful of agents that is customized to personal health, such as allergy and asthma patients, and to specific workspace, such as hospitals and paint factory. In this regard, our device is not just intended for research, but for a much wider usage base.

Exposome Compound Analysis Protocol

Compound Extraction
1. rescue adsorbent beads from the cartridge holder, the weight is about 200 mg for holder of 13 mm in diameter.
2. Add 1 ml methanol (MassSpec grade) to each, incubate for 20 min at room temperature. Then spin at 22,000×g for 20 min at RT. Take the supernatant as the metabolite extract.
3. For LC-MS analysis, the metabolite extract was transferred to 150-µl deactivated glass insert housed in Waters 2-ml brown MS vials.

Variations
1. methanol may be mixed with water at various concentrations, e.g. 50-100% to achieve optimal extraction efficiency.
2. The type and amount of adsorbent may also be changed after further technical development LC/MS Acquisition LC/MS analysis was performed in a platform that has Waters UPLC-coupled Exactive Orbitrap Mass Spectrometer (Thermo, Waltham, Mass., USA), using a mix-mode OPD2 HP-4B column (4.6×50 mm) with a 4.6×10 mm guard column (Shodex, Showa Denko, Tokyo, Japan).

The column temperature was maintained at 45° C. The sample chamber was maintained at 4° C.

The binary mobile phase solvents were: A, 10 mM $NH_4OAc$ in 50:50 Acetonitrile:water; B, 10 mM $NH_4OAc$ in 90:10 Acetonitrile:water. Both solvents were modified with 10 mM HOAc (pH 4.75) for positive mode acquisition, or 10 mM $NH_4OH$ (pH 7.25) for negative mode.

The flow was set as: flow rate, 0.1 ml/min; gradient, 0-15 min, 99% A, 15-18 min, 99% to 1% A; 18-24 min, 1% A; 24-25 min, 1% to 99% A; 25-30 min, 99% A.

The MS acquisition was in profile mode and performed with an ESI probe, operating with capillary temperature at 275® C., sheath gas at 40 units, spray voltage at 3.5 kV for positive mode and 3.1 kV for negative mode, Capillary voltage at 30 V, tube lens voltage at 120 V and Skimmer voltage at 20 V. The mass scanning used 100,000 mass resolution, high dynamic range for AGC Target, 500 ms as Maximum Inject Time and 70-1,000 m/z as the scan range.

Variations

The LC and MS systems and LC columns for future use are not limited to the brands mentioned here.

LC/MS Data Analysis

Post-Acquisition Analysis

The raw LC/MS data files were centroided with PAVA program (Guan et al. *Mol. Cell Proteom* 2011) and converted to mzXML format by an in-house R script (distribution upon request). Mass feature extraction was performed with XCMS v1.30.3. The mass features were then manually searched against the Metlin metabolite database using 5 p.p.m. mass accuracy. Retention time matching with compounds in the standard mixture was also performed for a portion of the metabolite hits. The scored mass features were clustered with SIMCA v14.1 (Umetric, Malmo, Sweden).

Variations

The software XCMS and SIMCA, database Metlin may have new versions or new content.

Results: Molecular Sieve Adsorbents are Capable to Capture Volatile Organic Compound Two natural compounds characteristic of orange flavor were detected from adsorbent extraction, but not from adsorbents that were not incubated with orange peel. The identities of both compounds were validated later with compound standards. Each sample has 6 technical replicates.

To find the optimal adsorbents to capture the air-soluble compounds in the environmental exposure, we reasoned that a hydrophobic surface is needed because of the volatility of these compounds. The molecular sieve adsorbents we tested are made of zeolite 13X, a type of aluminum oxide materials with nanometer-scale pores. The huge surface exchange area at 515 $m^2/g$ and the small bead size (45-60 mesh) make zeolite 13X a great choice for volatile molecule capturing and for ease of handling. In the industry, zeolite-base molecular sieve materials are used as gas molecule partitioning, such as gas chromatography, or to remove small molecule impurities during petroleum refining (hence the name).

From the results shown above, we demonstrated the zeolite molecular sieve materials can be used to capture volatile organic compounds. We then designed and 3D-printed holder cartridges filled the zeolite 13X and tested its performance in real life.

Results: Unexpected Workspace Exposure to Insect Repellent DEET

Figure 13A:
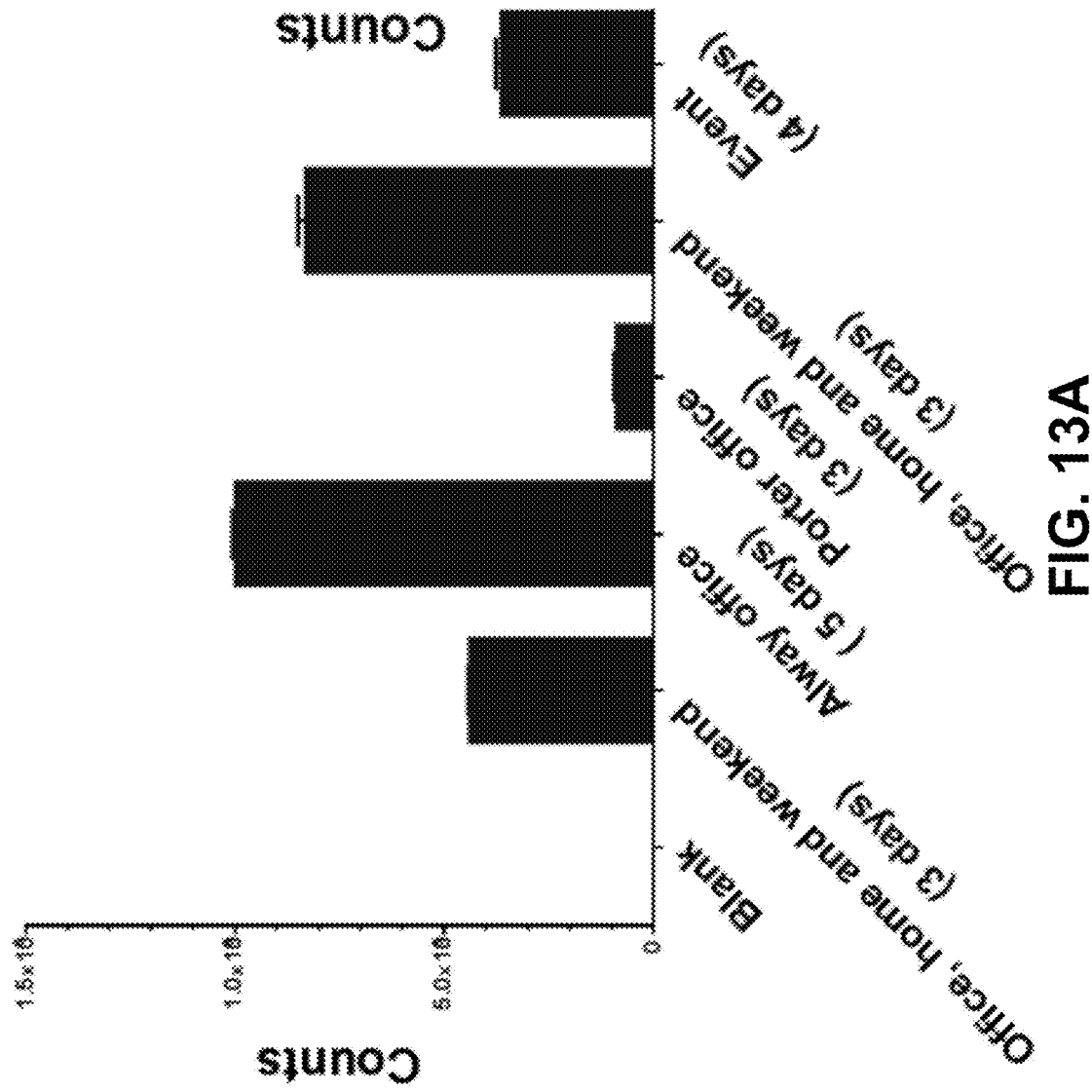
FIGS. 13A-B show according to an exemplary embodiment of the invention levels of diethyltoluamide (DEET) levels from environment exposure samples collected with the zeolite 13X adsorbents.
Figure 13B:
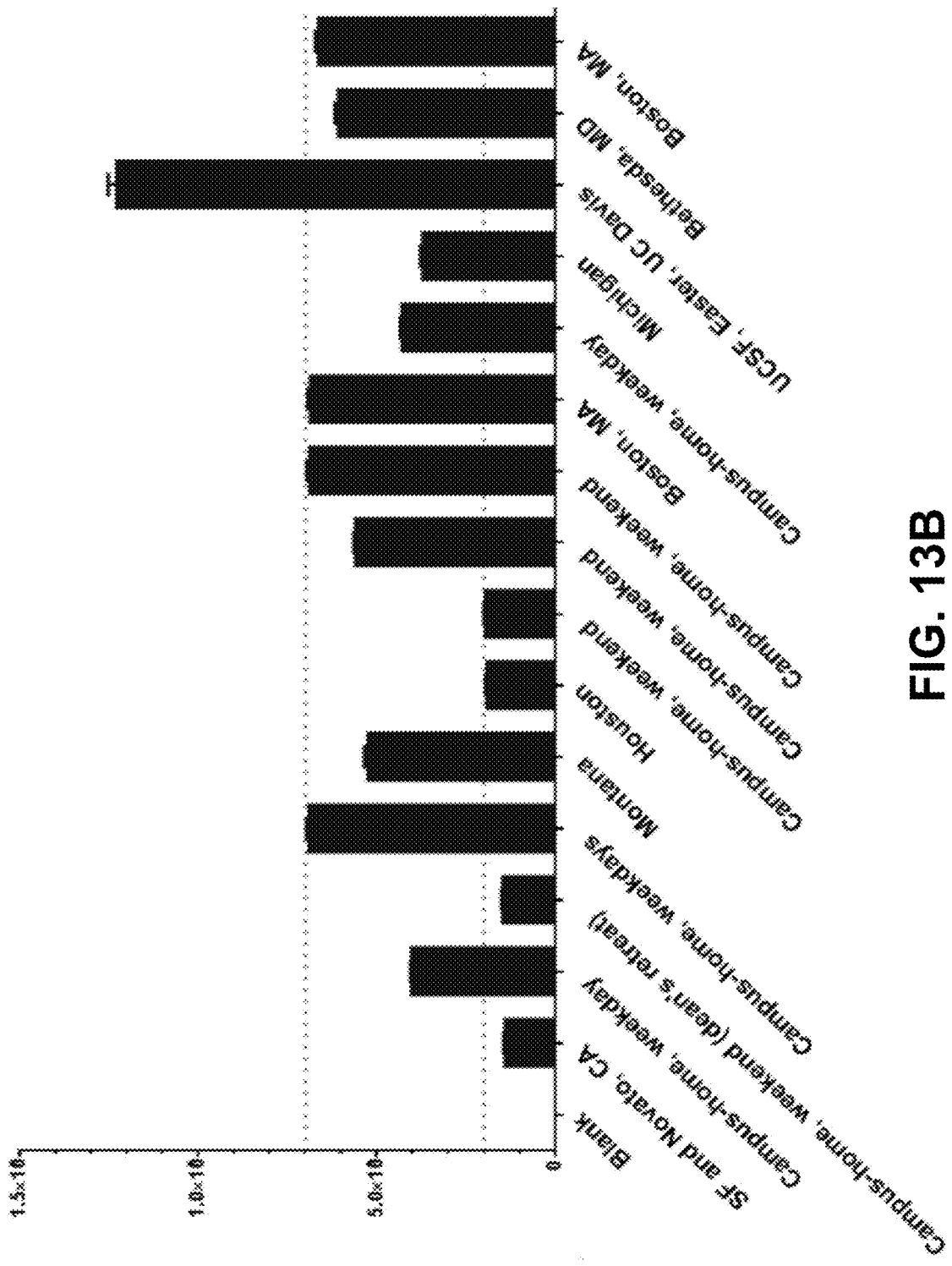

FIGS. 13A-B shows levels of diethyltoluamide (DEET) levels from environment exposure samples collected with the zeolite 13X adsorbents. Compared with its absence in the blank (extract from unused adsorbents), DEET was detected in different work-life locations around us (Left). And its levels vary between an individual's trips to different locations (Right).

In a test, we analyzed the compounds captured with the zeolite X13-filled cartridges from routine locations. Unexpectedly, a wide-used insect repellant, DEET, was detected as a significant exposure ingredient. The levels range widely between locations. As shown on Left, our working space at Porter Drive, Palo Alto, has significantly lower levels than in Alway building on Stanford campus (4-10 fold difference). And when the collection location change to an event in Mountain View, the DEET level also drops. From a longitudinal track of DEET exposure from the same individual (Right), different geological locations varied by >11-fold.

After validation and deduction from a standard curve, we found the average maximum exposure to DEET may exceed 5 mg/week in real life. If the exposure occurs instantaneously, the actually exposure may far exceed the average level.

Although DEET is classified as Category III "slightly toxic" by the EPA, its long-term effects on human health is not well studied. However, the EPA instruction states to avoid direct contact or intake of DEET. Given its acute lethal dosage at 5 mg/L in rats and pervasive existence in our surroundings, DEET should be carefully monitored for its potential effects on public health.

Results: Pervasive Exposure to Harmful Compounds are Revealed by Comprehensive Environmental Exposome Profiling.

Figure 14A:
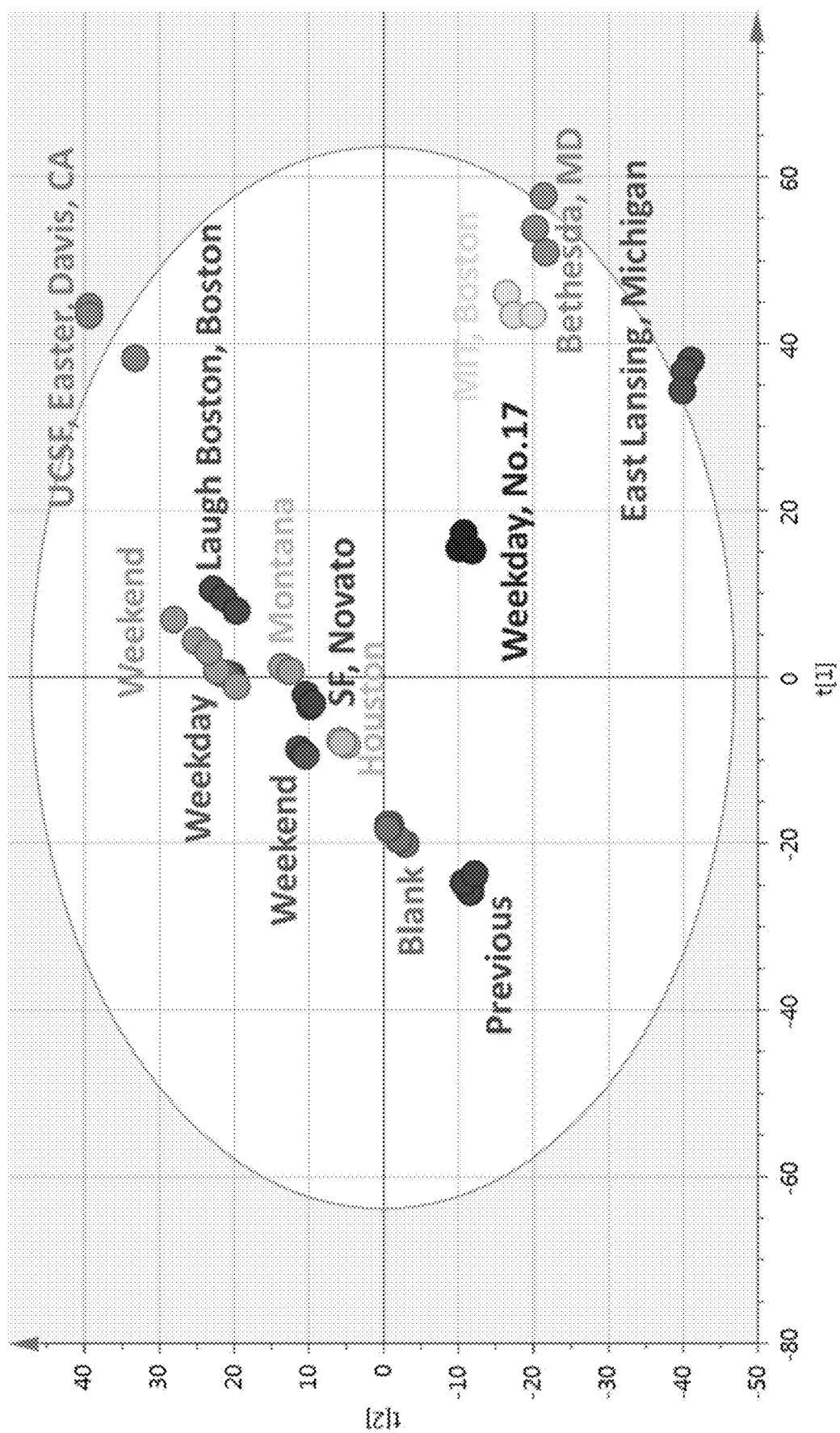
FIGS. 14A-B show according to an exemplary embodiment of the invention an analysis of the chemical exposure reveals unnoticed exposure that is specific by locations.
Figure 14B:
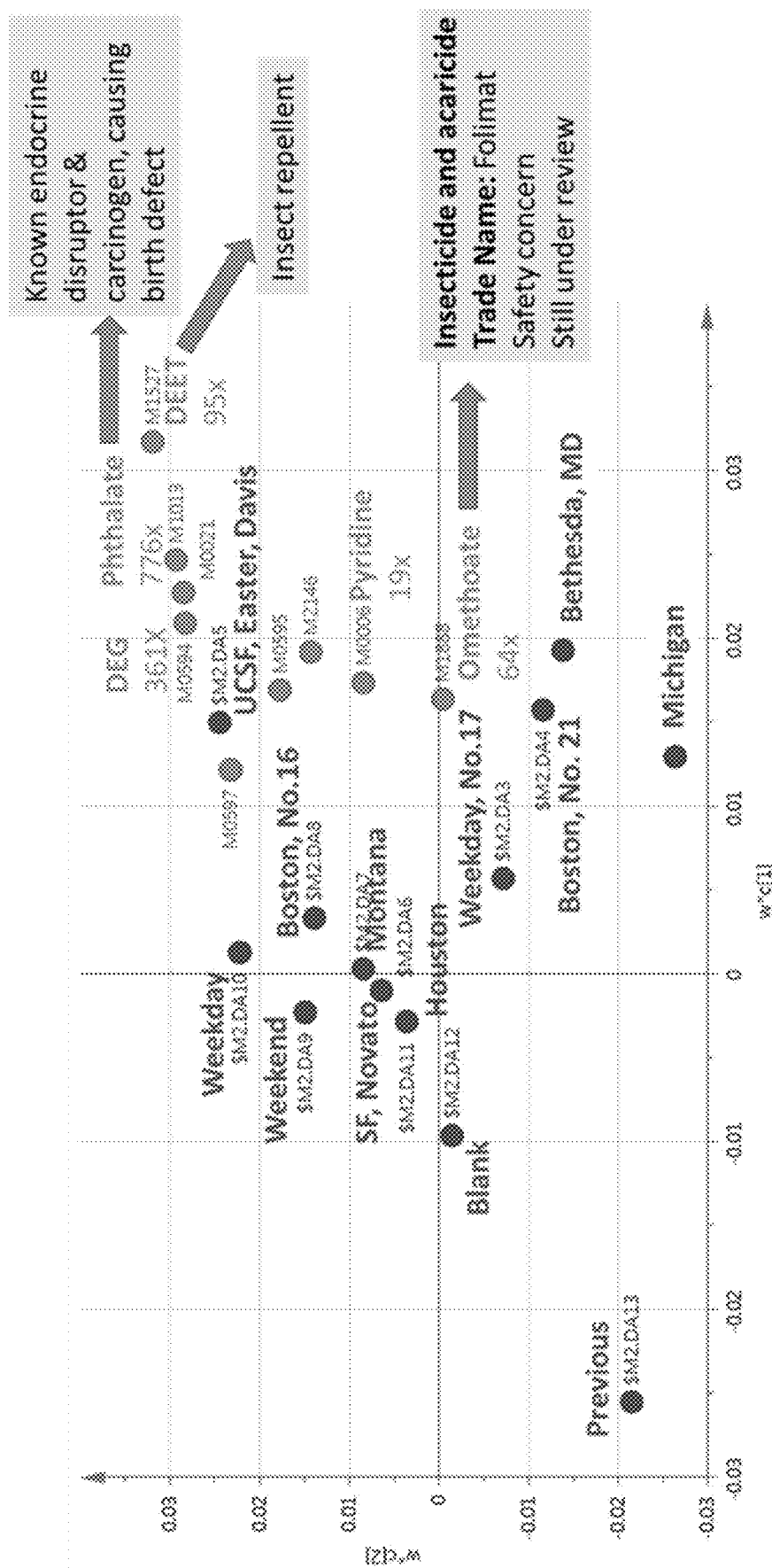

FIGS. 14A-B show a complete analysis of the chemical exposure reveals unnoticed exposure that is specific by locations. A longitudinal profile of an individual's personal exposome compounds (1968 features>10-fold enrichment) are clustered with a PLS-DA model by locations. Each sample has 3 technical replicates. Potential harmful compounds and their levels in each location are summarized. The levels of four representative compounds from the same batch of samples could be shown separately (not shown herein).

To investigate the environmental exposure on a personal scale, we profiled the compounds from exposome samples from an individual's real life from January to April, 2016. Over the period of 2.5 months. We collected 21 exposome samples over a wide range of geological locations in the United States. Their overall chemical composition was analyzed and showed great variation. Even for the two trips to Boston, which are in February and March and apart by 31 days, the exposome chemical profiles are very different, as shown by the vertical distance between these two groups. This difference is partly due to the two destination sites, one was at MIT while the other was in a club five miles away. This observation further demonstrated that the exposome profile is personal and should be analyzed with personal resolution.

Analysis of the chemical composition revealed several compounds of concern (FIG. 14B). These include phthalate, a known endocrine disruptor and carcinogen, and omethoate, an insecticide and acaricide that has not cleared regulations. Because our exposome samples were mostly collected from ordinary working and living sites, which did not involve any chemical manufacturing or regular use of these compounds to our best knowledge, the unnoticed exposure may raise serious concerns over neglected health risks. For example, a pregnant woman may be especially vulnerable to phthalate, a compound known to cause birth defect.

Appendix: Ultra-Sensitive and Universal Species Detection Pipeline for Next Generation Sequencing Data-Biotic Analyzer

SUMMARY OF THE APPENDIX

Provided is a presumption-free pipeline that employs experimental and analytic modules to profile samples, including clinical samples, regardless of the complexity and abundance (with unparalleled detection sensitivity down to single microbial cell level, equivalent to $\frac{1}{500}$ of a typical human cell in size and $\frac{1}{1000}$ in nucleic acid content).

This invention pertains to computer-implemented software method as a pipeline that includes a fully custom built genomic database and its accompanying taxonomy database. The pipeline uses the known search algorithm BLASTN to search DNA fragments against the fully custom built genomic database, and then uses an implementation we developed of lowest common ancestor (LCA) algorithm and the taxonomy database to classify fragments.

Experimental Module (Sample Extraction and Sequencing Library Preparation)

We have developed a streamlined procedure to process any samples for ultra-sensitive sequencing analysis. Starting from any samples that contain the microbial communities of interests, our experimental pipeline can efficiently break down any bacterial, fungi, plant, and animal cells, even when embedded in other scaffolds such like soil, human feces, and filters.

The pipeline allows concomitant extraction of DNA and RNA from a single sample. All reagents went through a thorough decontamination procedure to ensure minimal foreign contaminating DNA/RNA introduced. Based on the yield of the extraction step, we include an optional amplification step for both DNA and RNA. Specifically, for DNA, we perform isothermal multiple displacement amplification (MDA) adapted from single-cell studies. For RNA, we perform isothermal RNA linear amplification coupled with rRNA depletion. This is vastly more superior to the conventional mRNA fishing approach using the poly-A tail as a bait, as viral RNA (genomic vRNA) would not have those features. Finally, DNA and converted cDNA (from RNA) are subjected to an automatable single-tube protocol for efficient library preparation for the next generation sequencing (NGS) platform, the sequencing results of which are fed into our analytical module.

Analytic Module (Computer-Implemented Software Method)

Our analytical module is implemented as a computational pipeline that performs deduplication, quality control, in silico decontamination, assembly, and taxonomy classification. The taxonomy classification is achieved by the fully custom-built DARWIN database and the accompanying taxonomy database and our implementation of the lowest common ancestor (LCA) algorithm. The choice of database alone is the most important step in any taxonomy classification related studies, as it is much harder, if not impossible, to classify species that are simply not included in the database (or worse yet, misclassify them). For these reasons, we survey a broad spectrum of organisms spanning across all domains of life in our DARWIN database. To compensate for the potential long computational time due to the inclusiveness of the database, the analytic module includes three searching algorithms that have different trade-offs between time and sensitivity. In addition, we include a continue option for the CPU-intensive database searching step so the user could choose to resume this process in the events of unexpected interruption. Finally, the CPU intensive database searching step is deployable on Cloud Computing platform such like Google Cloud through virtual system encapsulations (docker images) to help with institutions/individuals who do not have access to the cluster computing engine, where the analytic pipeline was originally developed.

Independent Capability

It should be noted that our experimental and analytic modules can work independently of each other if the user so desired. The experimental module for ultra-sensitive DNA/RNA extraction and sequencing can be used to extract information from any samples to feed into analytical pipelines chosen by the user. Alternatively, the analytic module for universal species detection can be fed with data generated with other experimental pipelines and different sequencing platforms.

Applications

Our ultra-sensitive and universal species detection pipeline has very broad applications, even well beyond the original intended purpose—to study the human and environmental microbiome. In fact, since we survey all domains of life in our database, this pipeline is viable for analyzing extremely diverse biological samples:

Eukaryotic (animal/plants/fungi etc.) and/or prokaryotic (bacteria/virus etc.),
Single organism or a mixture of organisms,
Extreme low abundance or high abundance,
Free-living cells or trapped in scaffolds such as soil, feces, and filters etc.

Some outstanding examples are:
1. Diagnosing patients infected with unknown pathogens when conventional diagnosis have failed. In situations where the nature of the pathogen(s) is unknown, which could be bacteria, virus, fungi, protozoa, and parasite, or even as a mixture of several organisms, and the health of the patient is at stake, our pipeline provides a urgent one-stop solution to quickly help the medical practitioners to narrow their search range, if not directly identify the culprit(s).
2. Constructing comprehensive profiles of environmental risk factors in personalized medicine. Human diseases are essentially unfortunate consequences of intertwined genetic and environmental risk factors. By tailoring to individual needs, our pipeline can reveal the full spectrum of biotic environmental risk factors that may incite unwanted responses such like allergy and asthma and provide a complete risk factor map for activity guidance.
3. Implementing in epidemic surveillance on infectious microbial pathogens in public spaces. The majority of epidemic breakouts (or the unlikely events of bioterrorism attacks) are followed by intensive efforts to identify the pathogens from clinical labs, often in weeks or even months. Instead, we can implement our pipeline along with public sampling stations that provide constant surveillance over key traffic hubs or high population density areas. By analyzing the samples periodically or on demand, we can monitor, track, or even catch the developing epidemic situations, enabling quick epidemic intervention.
4. Improving agriculture yield by enhancing and modifying the host-microbiome mutualistic relationships. Humanity is constantly striving to improve the agricultural yield from our crops and livestock. Similar to the human-microbiome relationship, plants and animals also benefit tremendously from their respective microbial communities. Revealing and utilizing these host-microbiome relationships will undoubtedly increase the yield and disease resistance of crops and livestock. Our pipeline can provide a broad and unbiased summary on the said complicated host-microbiome relationships.

We attribute the following advantages to this invention:
1. The ability to extract nucleotide information from very low abundance samples ($10^1$ bacterial cell level) due to our strict decontamination protocols and unbiased amplification protocols.
2. The ability to classify species spanning all domains of life (broad range detection of highly diverse samples). Previous efforts usually only focus on a sub-domain of life, mostly bacteria, virus and maybe some fungi.

We could adapt our experimental pipeline to clinical samples where human tissues are dominant. On the other hand, our database is constantly updated and curated to cover all domains of life heuristically. Finally, a visualization module can be developed for the taxonomy report using open-sourced statistical software R.

In one embodiment, the invention is a pipeline detection with the following steps:

Deduplication, Quality Control, In silico decontamination, Assembly and Taxonomy classification, all implemented by software on a computer system or one or more computer processors. The steps can be regarded as computer-implemented steps executable on and by a computer system.

For Deduplication, the input to the pipeline is raw sequencing reads in fastq format from the sequencing platforms. The deduplication action or process pertains to removing exact paired-duplicated reads from the data. Sequences of each reads are directly hashed and compared to speed up the process. The output of the action or process is processed de-duplicated sequencing reads in fastq format.

For Quality control, the input is the processed de-duplicated sequencing reads in fastq format. The quality control action or process is to use e.g. software Trim_galore, which will remove any remaining sequencing adapters and low quality bases from the 5 prime and 3 prime ends. Trimmed reads shorter than 30 bp are removed all together. The output of the action or process is de-duplicated, trimmed high quality reads in fastq format.

For In silico decontamination, the input is de-duplicated, trimmed high quality reads in fastq format. The in silico decontamination action or process is that the processed reads are mapped to the human reference genome hg19 version by e.g. the bwa-mem algorithm. Reads mapped to the human reference genome are removed from the sequencing data. The output of the action or process is de-duplicated, trimmed, nonhuman reads in fastq format.

For Assembly, the input is de-duplicated, trimmed, non-human reads in fastq format. The assembly action or process is that the processed reads are assembled de novo using megahit using the metagenome-sensitive preset. The cut-off for DNA contigs are 300 bp, and 200 bp for RNA contigs. Anything shorter than the cut-off are removed. The output of the action or process is assembled contigs from the input reads.

For Taxonomy classification, the input is assembled contigs. The taxonomy classification action or process is that the assembled contigs are searched against a custom built database that covers all kingdoms of life, using e.g. the BLASTN algorithm. A wrapper was written to introduce the continue option and examine the integrity of the BLASTN results. The BLASTN results are parsed using custom-implemented LCA algorithm to achieve a balance between sensitivity and specificity of classification methods. The results are further parsed through a custom written taxonomy report script which generates taxonomy abundance information at all taxonomy levels, in addition to listing species separately for each kingdom of life. Finally, identity of contigs to reference genomes are retained and display at the species level to facilitate the confidence of taxonomy assignment. The output of the action or process is BLASTN results, LCA results, Taxonomy results.

In one embodiment, the invention is an experimental pipeline for pan-domain species nucleotide extraction and next generation sequencing library preparation. In this pipeline, the following steps are included:

preparing DNA/RNA genome libraries from collected metagenome samples at a single bioparticle sensitivity, wherein a radiation-based reagent-decontamination protocol is implemented to remove any traces of amplifiable nucleotides from reagents, wherein a sterilized hydrophobic or hydrophilic filter membrane is used to collect nano-gram-level amount of airborne biological particulates at the minimum in between 12 to 72 hours, wherein, with an amount range above 1 ng of nucleotides of airborne biological samples, extracting DNA and RNA concurrently from the collected samples of any nature by a chemistry/physics-based pipeline at a single bacterial particle sensitivity, wherein a non-PCR-based linear amplification technique is applied for DNA and RNA after converted to complementary DNA, and wherein, with limited RNAs, depleting most ribosome RNA with selective primers for preferential enrichment of non-ribosome RNA sequences; and using cocktail enzyme to fragmentize DNA/cDNA generated to minimize the loss of nucleotide materials.

In another embodiment, the invention is a pan-domain species detection bioinformatics pipeline for next generation sequencing data. In this pipeline, the following steps are included, which are executed by a computer or one or more computer processors:

building a non-redundant genome sequence database incorporating publicly available genome sequences and/or select organisms of interest;

building a taxonomy database to store taxonomy information for every sequence in the database;

creating de-duplicated sequencing reads in fastq format by removing exact paired-duplicated reads from raw sequencing reads;

trimming the de-duplicated sequencing reads;

mapping the trimmed de-duplicated sequencing reads to a human reference genome therewith creating trimmed de-duplicated non-human reads in fastq format;

creating assembled contigs from the trimmed de-duplicated non-human reads in fastq format by a rigorous reads assembly method with specific parameters to minimize chimeric assembly;

classifying the assembled contigs by searching against the non-redundant genome sequence database; and outputting the classified results.

DETAILED DESCRIPTION OF THE APPENDIX

Definitions

Next-generation sequencing (NGS), also known as high-throughput sequencing, is a catch-all term used to describe a number of different modern sequencing technologies including:

Illumina (Solexa) sequencing

Roche 454 sequencing

Ion torrent: Proton/PGM sequencing

SOLiD sequencing

These technologies allow us to sequence DNA and RNA much more quickly and cheaply than the previously used Sanger sequencing, which is the main reason we are calling it "next generation sequencing". The massively parallel sequencing technology known as next-generation sequencing (NGS) has revolutionized the biological sciences. With its ultra-high throughput, scalability, and speed, NGS enables researchers to perform a wide variety of applications and study biological systems at a level never before possible.

Ultra-sensitive is a term relevant to our experimental part of the invention, where we show that the pipeline is able to extract sufficient information from 10 bacterial cells and 200 viral particles.

Universal is a term relevant to our custom-built databases, which aim to characterize species from all kingdoms of life, including, but not limited to, bacteria, fungi, viruses, plants, animals, archaea, etc.

Overview

The experimental pipeline of this invention is unique in that it is adapted to single-cell level amount of nucleic acids materials from a mixture of diverse organisms. It is noted that it also works if more materials are provided. The details of the steps of pipeline are provided in the Experimental Protocols section. Traditionally, single-cell experiments are only carried out in mammalian cells or bacterial cells where single or a few cells of the same species are processed at a time. The experimental pipeline aims to process a diverse mixture of organisms presented in a very small amount of materials (equivalent or less than 1000 microbial cells, which is about single mammalian cell level for materials). This seemingly contradictory situation requires novel experimental and analytical techniques to faithfully deconvolve the population structure. Therefore, preserving the signatures from diverse organisms and reducing the impact of contamination from either human or reagent sources becomes a paramount task to accomplish.

Decontamination Methods

To this end, we employ rigorous reagent selections and specific in-lab decontamination protocols. Specifically, we have tested majority of commercially available microbiome extraction kits and adopted the one that has the following two traits: 1, efficiently breaking diverse organisms' cells and releasing the nucleic acid contents, 2. high reproducibility and minimal material loss when only a small number of cells are provided (According to the supplier, the use of their kit for such a small number of cells were never done and they consider it impossible). Upon receiving the extraction materials, we then aliquot all reagents that do not contain enzymes into 1.5 ml plastic tubes and place them around 3 cm from the 254 nm UV radiation source inside a commercial Stratalinker 2400 UV CROSSLINKER for 30 minutes (4000 mwatts/cm$^2$). The amount of UV energy exposed is at least twice as much as required to break at least 99.9% contaminating nucleic acids in the reagents to sub-73 bp (Plos ONE), which should have minimal impact on the downstream amplification and library preparation steps. In addition, all personnel are required wear long-sleeve lab coats and face masks, working in a physically separated and designated clean hood when performing the extraction process to minimize human contamination. In a possible variation, the exact amount of UV light exposure and the volume of each aliquot can be adjusted for larger scale of operations.

The successful outcome of decontamination is reflected in the qPCR quantitation results (for these results see priority documents(s)). DNA extraction was performed without the strict decontamination protocol. We found that DNA extracted from 10$^3$ E. coli cells yield virtually no difference in amplification curve when compared to No Template Control (NTC, i.e., DNase-free water). This suggests that the E. coli DNA signals are completely masked by the inherent contaminating DNA (bacterial origin) in the reagents. In comparison, when strict decontamination protocol is implemented, while the amplification curve of 10^3 E. coli cells remain mostly unchanged, the amount of DNA in NTC is no longer detectable (cycle>34-35 is considered sub-single molecule level). These results strongly underscores the importance of our strict decontamination protocol prior to handling materials with extremely low amounts of nucleic acids.

Amplification Methods

The amount of DNA and RNA extracted from our samples are usually in such low quantities that machines such as NanoDrop and Qubit are unable to measure. Thus, the second technological hurdle to overcome is to amplify the nucleic acids to a level where sequencing libraries can be prepared. Commercially available next generation sequencing (NGS) library preparation kits require minimum 1 ng input, which is approximately 1000× more than the amount we obtain from extraction. To this end, we utilize a single-cell Multiple Displacement Amplification kit to amplify DNA. For RNA, a single primer isothermal amplification kit specifically designed to amplify all non-rRNA is used. As most RNA amplification kits are tailored to mRNA, which selectively enrich for RNA that contain poly-A tail, they are unsuitable for our case. This is because almost all bacterial and viral RNA do not have poly-A tail and therefore will not be amplified. Thus, selecting the broad amplification of all non-rRNA technique is important and will preserve the complex community structures of our samples. Following amplification, DNA and cDNA are converted into sequencing libraries using commercially available kit for next generation sequencing (NGS).

Sensitivity of Detection Methods

To test the sensitivity of our pipeline, we titrated E. coli culture down to 1000, 100, and 10 cells and extracted these samples using our pipeline, along with a blank control to monitor the contamination background. Our results show that our pipeline can accurately detect at least down to 10 E. coli cells from the sample (FIG. 2). This is surprising because conventional extraction methods are catered to extracting bacterial DNA from at least millions of cells. It is most certainly unexpected that our pipeline can also work with minimal input cells and provide good and reliable results (based on communication with senior scientists at company that manufactures the extraction kit).

Spiked-In Evaluation of the Amount of Materials Collected

Figure 3A:
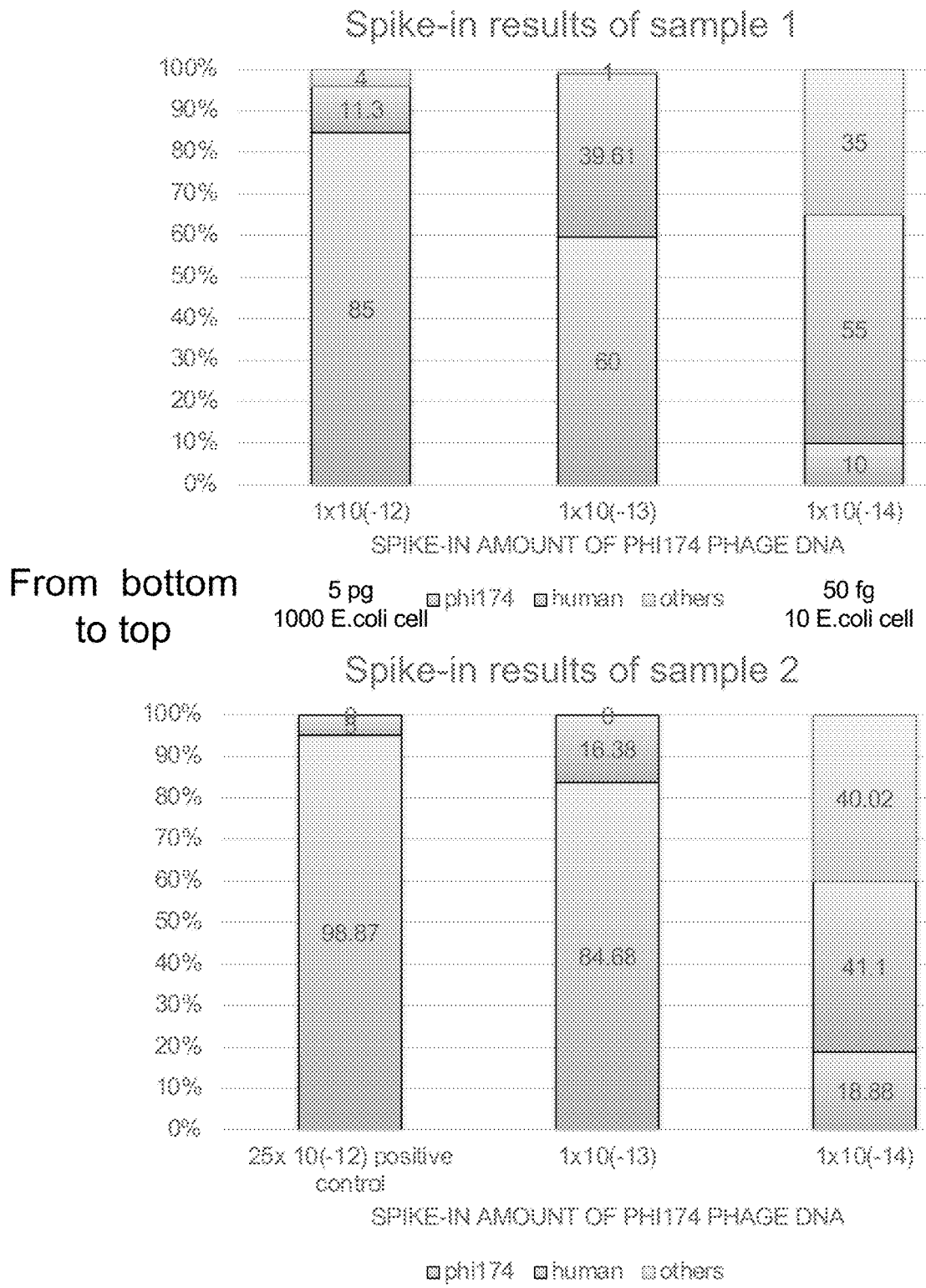
Figure 3C:
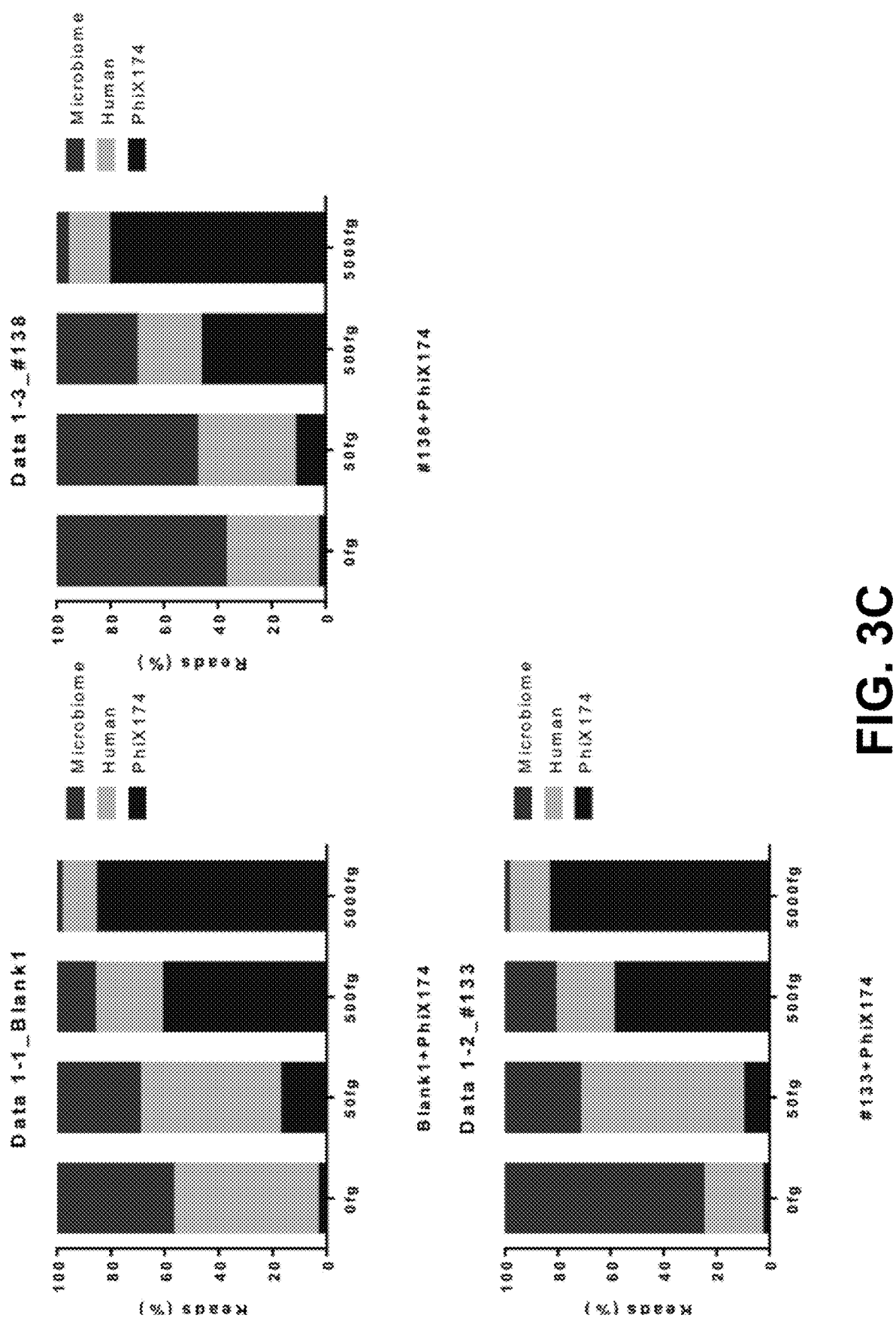
Figure 4:
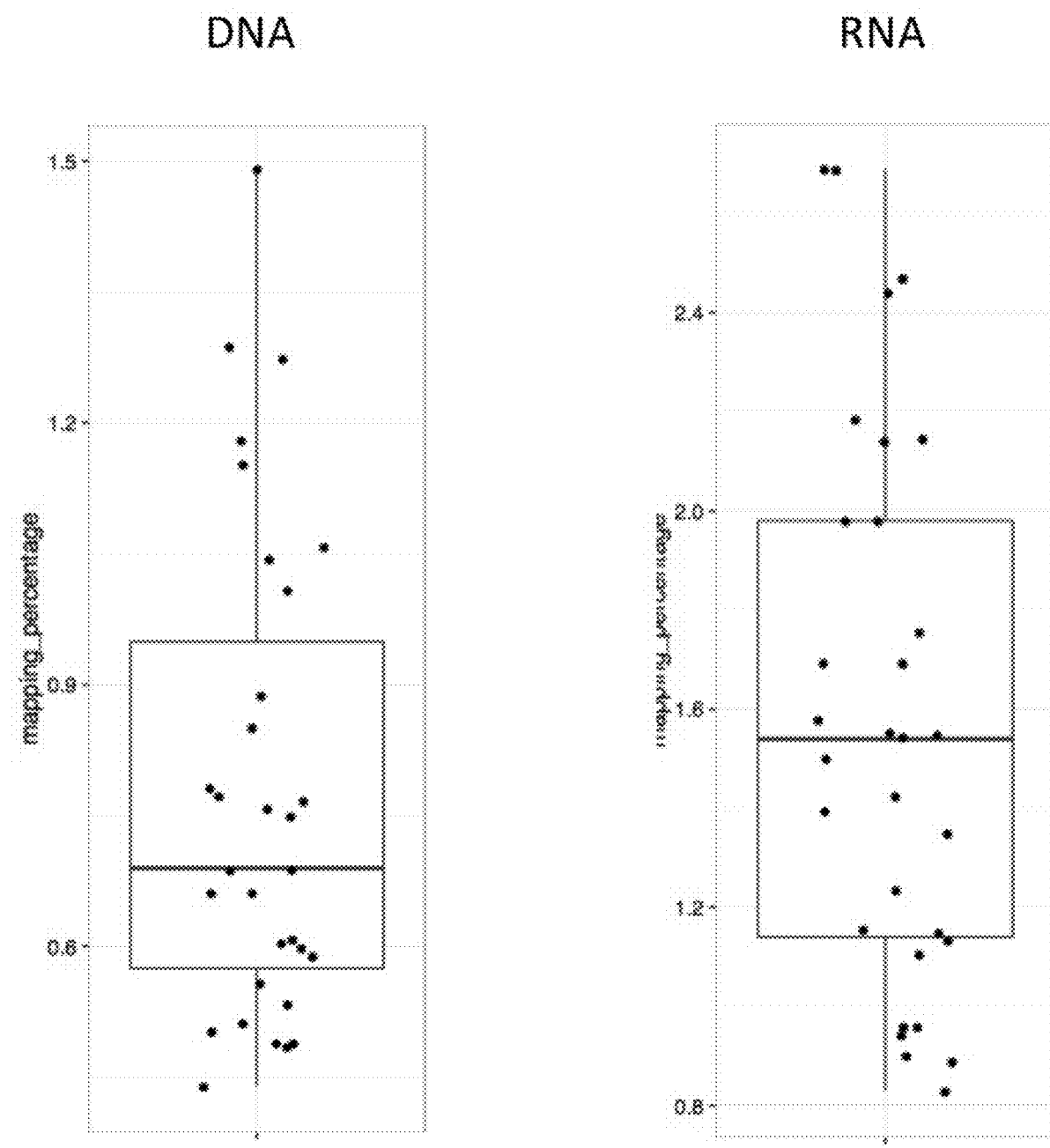
FIG. 4 shows according to an exemplary embodiment of the invention minimal amount of reads map to Phi174 in actual samples.

We also precisely evaluated the actual amount of nucleic acids content in situations where extremely small amount of sample are collected (samples collected from a personal device as disclosed in U.S. Provisional Application 62/488, 256 filed on Apr. 21, 2017 and 62/617,471 filed on Jan. 15, 2018). To gather samples for this part, we used commercialized RTI device which was intended to collect pollutants on a filter through active sampling from air and measure them using mass-spectrometry. Adapting this strategy, we instead extract biological contents from the filters using our pipeline. To our knowledge, there are no direct methods to reliably measure nucleic acids amount at sub-pg ($<10^{-12}$ g) levels, thus we resort to amplification and sequencing. Prior to DNA amplification, a known amount of E. coli phage PhiX174 (5 pg, 500 fg, and 50 fg) is spiked into our sample (in triplicates). The spike-in serve as "ballpark estimates" of the amount of materials initially present. Since our protocol uses random amplification, it is reasonable to assume the final amount ratio between our sample and PhiX174 reflects the actual amount collected. Post-sequencing, the sequencing reads are mapped to human and PhiX174 genomes. Sequencing reads that are non-human and non-PhiX174 are labeled as "others". The number of reads in each category are represented as a percentage of the total reads (FIGS. 3A-B). As shown, there is considerable contamination from human resources, as always expected. In ideal cases, if the initial amount of our sample is the same as the spiked-in PhiX174 DNA, the ratio between reads mapped to "others" and PhiX174 should be 1:1. This "others"-to-PhiX174 reads ratio is expected to change proportional to the initial DNA amount in our sample versus spiked-in PhiX174. At 50 fg of PhiX174 DNA, we noticed that "others"-to-PhiX174 reads ratio are approximately 2:1 for both sample 1 and 2, suggesting that our sample contains more than 50 fg of DNA initially. Increasing PhiX174 (blue) spike-in amount to 500 fg (or $5\times10^{-13}$ g) is sufficient reduce the percentage read of "others" to almost 0. These results suggest that our original extracted amount (samples 1 and 2) are between the range of 50 fg-500 fg, equivalent to 10-100 E. coli cells. This assessment is in agreement with our sensitivity evaluation from FIG. 1. Similar conclusions can be drawn from the RNA spike-in samples and tests as well (FIG. 3C). It is known RNA is less stable than DNA when exposed to environment, which may underestimate the actual number of cells collected. Finally, it is worth noting that we rarely detect PhiX174 in actual samples collected, as shown for both DNA and RNA in FIG. 4, and hence was chosen as the spike-in material in our experiments.

Detection is Highly Reproducible

Last but not the least, with our rigorous optimizations, our pipeline is highly reproducible. This is demonstrated by our results where the extraction and processing of two air samples collected side by side show up to 0.9 correlation coefficient at the species level (for these results see priority document(s)).

Analytical Pipeline Descriptions and Supporting Analyses

Figure 5:
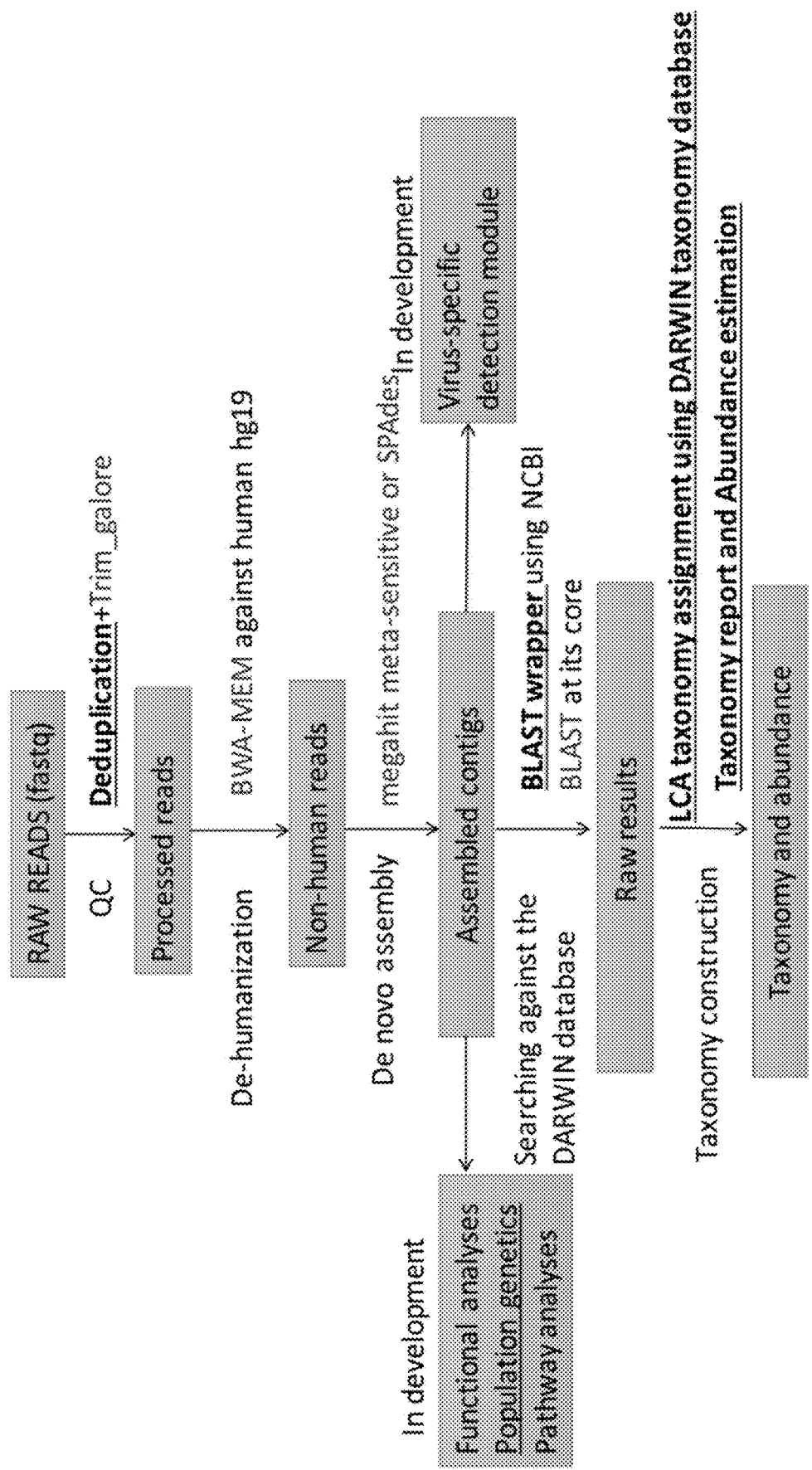
FIG. 5 shows according to an exemplary embodiment of the invention an overview of the analytical pipeline.

The analytical pipeline, or Universal Fragment Classification (UFC) pipeline, is a collection of scripts written in shell and python (FIG. 5). For certain tools, such as BLASTN, a wrapper is written to add a few functionalities into the BLASTN package which are essential for the scope of the analysis. This includes automatically splitting input for massively paralleled database searching and associated output parsing, automatic evaluation of the input and output to see if the results are complete, and a resume option in cases where prior searching step were interrupted due to unforeseen circumstances. Searching tens or hundreds of thousands of contigs of nucleic acids through a massive database (the DARWIN database) is a very time consuming and computing-extensive job, therefore careful optimizations need to be done to ensure the running time for each sample is within reasonable time-frame. The detailed descriptions of each step are described below.

The Detailed Steps of the Pipeline

DEDUPLICATION—Amplified DNA or RNA samples frequently suffer from data quality issues where abnormally high coverage of certain regions of genome/transcriptome are observed. This is due to the technical nature of amplification techniques. Conventional approaches attempt to first map reads to reference genomes and use the mapping coordinates to determine if they are duplicates. While memory-efficient, this approach is impossible for most microbiome research because such reference genomes simply do not exist. Therefore, an implementation of reference-free deduplication method is introduced in this pipeline. A possible variation is that the program can be rewritten in C++ for extremely large input size.

TRIMMING AND QUALITY CONTROL—This step is carried out using Trim_galore wrapper, which essentially combines the adapter removal tool Cutadapt and NGS quality control tool Fastqc.

DEHUMANIZATION—This step is performed using publicly available BWA-mem algorithm to map all reads to the human reference genome. The purpose is to remove the human reads portion (which is always present when samples need to be amplified before library prep, possibly from the sample handler) from the total reads so that the following assembly step is more efficient. A possible variation is that different version of human reference genome could be used and may yield slightly different results.

DE NOVO ASSEMBLY—This step can be executed either by Megahit or SPAdes, both of which are popular de novo de bruijn graph assembler for short read NGS sequencing reads. The purpose of this step is to assemble millions or more reads into separate information-dense "contigs", similar to piecing jigsaw puzzles together into bigger clusters. This is an essential step in this pipeline because of its role in data reduction and information retention, thereby increasing confidence in the subsequent taxonomy assignment (longer sequence=better confidence in assignment). A possible variation is that the choice of assembly algorithms and parameters are subject to change depending on the length of reads.

SEARCHING AGAINST THE DARWIN DATABASE—This step is carried out using a BLASTN wrapper, which takes NCBI BLAST as its core and adding functionalities that are essential to the pipeline. The BLAST algorithm is selected for this purpose because it remains the most sensitive algorithm to identify a given DNA/RNA sequence. Different BLAST algorithms can be specified by user depending on the size of input or sensitivity requirements of the analysis.

Figure 6:
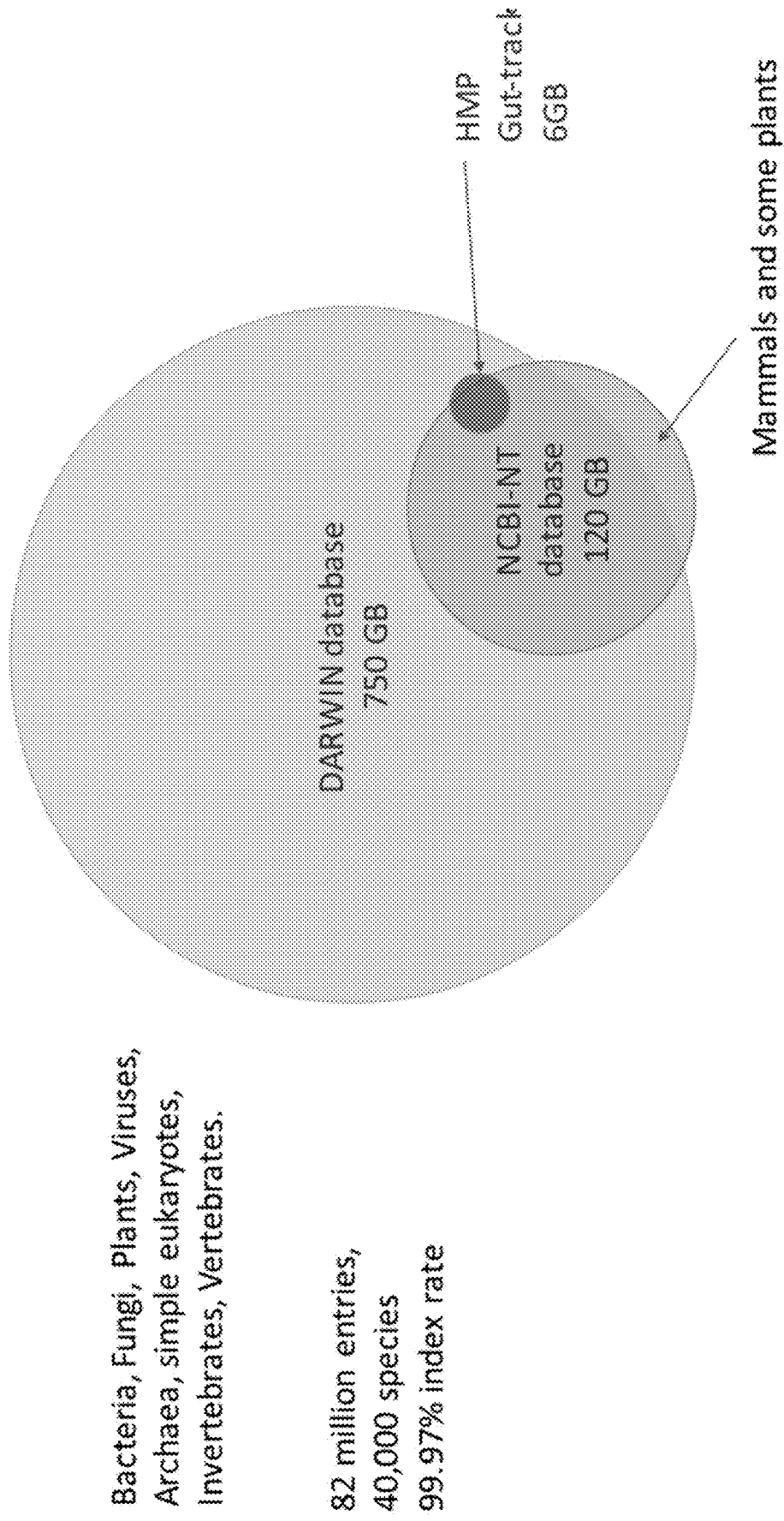
FIG. 6 shows according to an exemplary embodiment of the invention the Darwin database.

The choice of database(s) is the most crucial component when it comes to nucleic acids detection and classification. This is because alignment or mapping algorithms use these so-called reference sequences to identify reads or fragments. A poorly chosen database always leads to under-classification and sometimes even false-classification. Unless the sequences are very similar, it is fundamentally impossible to identify a group of species that are not included in the database (for example, a bacteria database can hardly detect any fungi). Thus, for accurate identification of organisms, a broad database encompassing all domains of life is essential. In addition, the database needs to be carefully curated. Unfortunately, public databases are often non-curated, which often translate into redundancy, low-quality, and sometimes contaminating data (especially in cases where one species live within another). We've addressed these issues by creating the DARWIN database. This database is an extensively expanded version of the NCBI BLAST NT database, which is hosted by the national center for biotechnology information (NCBI) containing nucleic acid information that represents all domains of life. However, unlike NCBI BLAST NT, which focuses more on the broad human health related organisms, DARWIN was created to better represent all domains of life (FIG. 6). This includes public and semi-public sources including the NCBI RefSeq database, Genebank database, and JGI portal expert version. Moreover, the data represented in DARWIN are carefully curated. The most current version of this curated database includes all domains of life known to humans, which are broadly divided into the following categories: plants, protozoa, invertebrates, bacteria, archaea, fungi, virus, non-mammal vertebrates and some selected animals (82 million entries, 40,000 species). A possible variation for the DARWIN database, while described here in a holistic way, can be separated into several domains of life based on which searching operations can be performed with specific focus and much faster computing time.

TAXONOMY ANALYSIS WITH LCA METHOD—The BLAST results from previous steps only provide an overview of what sequences may be, as provided in a list of potential organisms ranked by a statistical measure called e-value. However, consideration has been given to this process and simply picking the one with best e-value is not robust enough. Instead, a phylogeny inspired algorithm called Lowest Common Ancestor (LCA) algorithm is preferred. In our analytical pipeline this algorithm is implemented along with special considerations to certain domains of life that do not conform to usual taxonomy database structures. Accompanying the DARWIN database, a DARWIN taxonomy database specific to the DARWIN database (and beyond) is also constructed. The goal of taxonomy database is to provide a unique taxonomy label to each entry in the DARWIN database, which enables fast and accurate evaluation of taxonomy in the LCA step. In practice, a noticeable amount of contigs can be unexpectedly assigned to species belonging to different domains of life at the same time, hinting a possible contamination source in even well curated databases. This conflict of assignment can be easily ignored if the database does not contain species from different domains of life. A possible variation can be that the exact rule of assignment is modified depending on further optimizations.

TAXONOMY REPORT AND ABUNDANCE ESTIMATION—The inferred taxonomy results from the LCA step is compiled and displayed in human readable format. Specifically, the report follows the hierarchical taxonomy rank conventions of NCBI and display the sequencing abundance of each taxonomy rank in aggregate. Abundance estimation is handled in two approaches, median copy number of contigs assigned to each species and aggregate sequencing amount, which reflect different focuses of the analysis. The final report also includes a special section where species belonging to different domains of life are listed separately so one can quickly inspect domains of their interests. A possible variation is a graphic module where results from this step are made into standardized figures can be introduced.

UFC Pipeline Detects Significantly More Species than Conventional Methods

Figure 7:
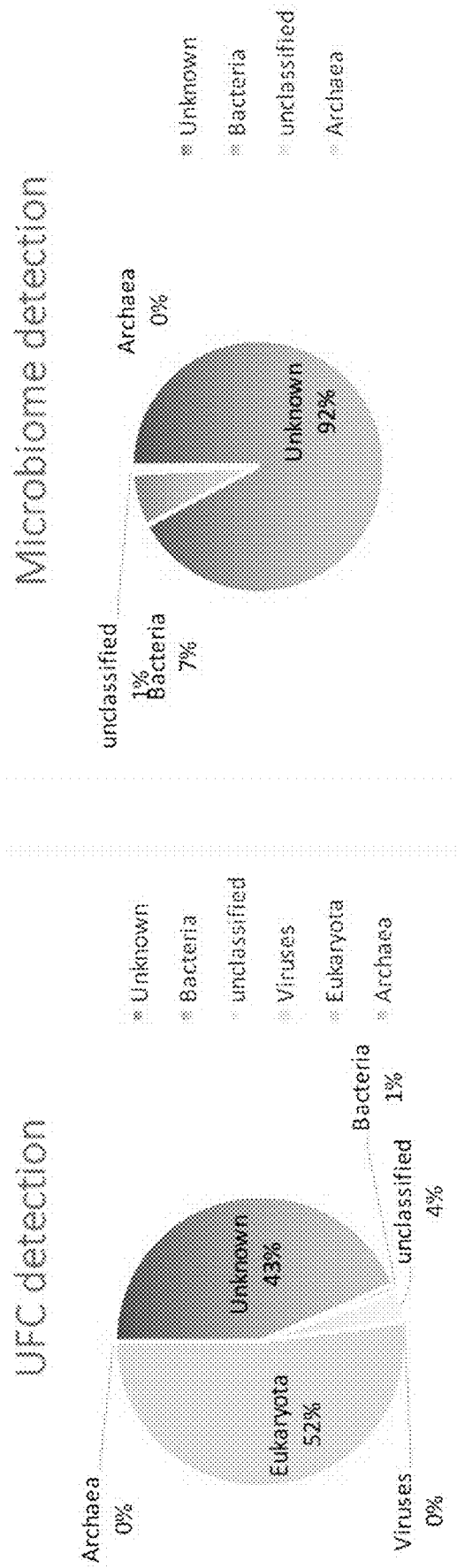
FIG. 7 shows according to an exemplary embodiment of the invention UFC providing complete coverage of organisms that are not covered by conventional microbiome package (to the extent of human knowledge).

Side-by-side comparison shows that the performance of our analytical pipeline can identify far more (53% against 7% in the example provided, but in cases where samples are dominated by plants, the percentage can be as drastic as 95% against 3%) portions of sequencing information than conventional packages (FCP package is compared here, FIG. 7). For RNA sequencing results the UFC can even identify up to 99% of sequencing information.

UFC Pipeline Detects Most Spiked-In Viral Species in a Complex Mock Mixture Sample Furthermore, in a mock community where we mix a panel of 12 different pathogenic viruses with bacteria and yeasts, we can reliably detect almost all viruses in the mixture despite their genome size being extremely small compared to bacteria and yeast (FIG. 8). If fact, we were able to detect viruses down to $10^2$ copies, equivalent to only $\frac{1}{10}$ of a *E. coli* cell, in a mixture of organisms, simulating a likely real-life scenario.

UFC Pipeline Detects Opportunistic Pathogens and Human Related Pathogens in Real Samples The final demonstration of the process of the pipeline is reflected by the analysis on more than 100 actual samples as a part of an academic study, where different species covering all domains of life can be detected with dynamic abundance. Several opportunistic pathogens and even a parasite in one case can be detected from the samples (for these results see priority document(s)).

Experimental Protocols

Simultaneous Biotics DNA and RNA Extraction

Filters captured the biotics samples were used for simultaneous DNA and RNA extraction by combination and modification of MO Bio PowerWater DNA and PowerWater RNA extraction kit. We altered the original protocols to allow extraction of DNA and RNA from the same sample.

Detailed extraction protocol is as follows:
4. Before start extraction, use RNA-free reagent to clean the processing surface in the hood.
5. Warm PWR1 at 55 degrees Celsius for 10 min. Aliquot 990 ul PWR1 (mix well to make sure have the precipitate in the tube) to 1.5 ml tubes, UV-treat for 1800 sec (30 min).
6. Select 7 sample filters and 1 blank filter as negative control. Insert the filter into the 5 ml PowerWater® Bead Tube.
7. Add 10 microliters β-mercaptoethanol (βME) to PWR1. Add 1 ml of Solution PWR1 containing PME to the PowerWater® Bead Tube.
8. Make sure cap is securely tightened on PowerWater® Bead Tube. Secure the PowerWater® Bead Tube horizontally to a MO BIO Vortex Adapter. The tube caps should be oriented pointing toward the center of the Vortex Adapter.
9. Vortex at maximum speed for 5 minutes.
10. Centrifuge the tubes≤4000×g for 1 minute at room temperature.
11. Transfer all the supernatant to a clean 2 ml Collection Tube. Draw up the supernatant using a 200 microliters pipette tip by placing it down into the beads.
12. Centrifuge at 13,000×g for 1 minute.
13. Avoiding the pellet, transfer the supernatant to a clean 2 ml Collection Tube.
14. Add 200 microliters of Solution PWR2 and vortex briefly to mix. Incubate at 4 degrees Celsius for 5 minutes.
15. Centrifuge the tubes at 13,000×g for 1 minute.
16. Avoiding the pellet, transfer the supernatant to two clean 2 ml Collection Tube (For DNA and RNA extraction). Expect to recover 800-850 microliters of supernatant (400-425 microliters each for DNA or RNA extraction).

For DNA extraction please follow Step 14 to 23. For RNA extraction please follow Step 24 to 39.

DNA Extraction Steps:
17. Add 325 microliters of Solution PW3 and inverse-mix by hand (no vortex) briefly.
18. Load 500 microliters of supernatant onto a DNA Spin Filter and centrifuge at 13,000×g for 1 minute. Discard the flow through and repeat until all the supernatant has been loaded onto the DNA Spin Filter.
19. Place the DNA Spin Filter basket into a clean 2 ml Collection Tube.
20. Shake to mix Solution PW4 before use. Add 600 microliters of Solution PW4 and centrifuge at 13,000×g for 1 minute.
21. Discard the flow through and add 600 microliters of Solution PW5 and centrifuge at 13,000×g for 1 minute.
22. Discard the flow through and centrifuge again at 13,000×g for 2 minutes to remove residual wash.
23. Place the DNA Spin Filter basket into a clean 2 ml Collection Tube.
24. Add 52 microliters of Solution PW6 to the center of the white filter membrane. Make sure the drop of solution is thoroughly absorbed into the filter membrane. Incubate for 2 minutes at room temperature.
25. Centrifuge at 13,000×g for 1 minute.
26. Discard the DNA Spin Filter basket. Aliquot DNA in 3 DNA/RNA LoBind tube (15 microliters each) to avoid freeze-thaw cycle. Seal the tube with parafilm. The DNA is now ready for downstream application.

RNA Extraction Steps:
27. Add 325 microliters of Solution PWR3 and 325 µl of Solution PWR4. Then inverse mix by hand (no vortex) briefly. PWR3 and PWR4 is binding buffer optimized for RNA.
28. Load 600 microliters of supernatant onto a RNA Spin Filter and centrifuge at 13,000×g for 1 minute. Discard the flow through and repeat until all the supernatant has been loaded onto the RNA Spin Filter.
29. Shake to mix Solution PWR5. Add 600 microliters of Solution PWR5 and centrifuge at 13,000×g for 1 minute. Discard the flow through.
30. Centrifuge again at 13,000×g for 1 minute to remove residual wash.

31. Place the Spin Filter basket into a clean 2 ml Collection Tube.
32. Prepare the DNase I Solution, by thawing the volume of DNase I stock enzyme needed according to the number of samples. Per prep, combine 5 microliters of DNase I stock enzyme with 45 microliters of Solution PWR6. For 8 samples, add 405 microliters PWR6 to 45 microliters of DNase I stock enzyme (45 microliters aliquot).
33. To the center of the RNA Spin Filter, add 50 microliters of DNase I Solution (prepared by mixing 45 microliters of Solution PWR6 and 5 microliters DNase I stock solution.
34. Incubate at room temperature for 15 minutes.
35. Add 400 microliters Solution PWR7 and centrifuge the column at 13,000×g for 1 minute.
36. Discard the flow through and add 600 microliters of Solution PWR5 and centrifuge at 13,000×g for 1 minute.
37. Discard the flow through and add 600 microliters of Solution PWR4 and centrifuge at 13,000×g for 1 minute.
38. Discard the flow through and centrifuge again at 13,000×g for 2 minutes to remove residual wash.
39. Place the RNA Spin Filter basket into a clean 2 ml Collection Tube.
40. Add 52 microliters of Solution PWR8 to the center of the white filter membrane. Incubate for 2 minutes at room temperature.
41. Centrifuge at 13,000×g for 1 minute.
42. Discard the RNA Spin Filter basket. Aliquot RNA in 3 DNA/RNA LoBind tube (15 microliters each) to avoid freeze-thaw cycle. Seal the tube with parafilm. The RNA is now ready for downstream application.

DNA and RNA Amplification

Biotics DNA samples are linearly amplified by the QIAGEN REPLI-g single cell MDA amplification kit with modifications.
1. 5 microliters of DNA sample was used for the amplification.
2. Add 5 microliters buffer D1 to the DNA sample. Mix by gently vertexing and centrifuge briefly. Incubate at room temperature for 3 mins.
3. Immediately add 10 microliters stop buffer N1. Mix by gently vertexing and centrifuge briefly.
4. For each reaction of 20 microliters denatured DNA, add 29 microliters of REPLI-g sc Reaction Buffer and 2 microliters REPLI-g sc polymerase.
5. Incubate at 30 degrees Celsius for 8 h.
6. Amplified product is cleaned using 1.8× volumes of the Agencourt XP beads to remove reagents from amplification step. Products are washed twice with 80% Ethanol. The final product is ready for library preparation.

Biotics RNA samples are linearly amplified by NuGEN Technologies, Inc. Ovation RNA-seq system V2 with modifications.

Step-1: First Strand cDNA Synthesis
1. Add 2 microliters of Al (First Strand Primer Mix) to a 0.2 ml PCR tube.
2. Add 5 microliters of RNA sample to the primer.
3. Place the tubes in a pre-warmed thermal cycler at 65® C. for 2 min and hold at 4 degrees Celsius.
4. Prepare a master mix by combining 2.5 microliters of A2 (First Strand Buffer Mix) and 0.5 microliters of A3 (First Strand Enzyme Mix) in a 0.5 ml capped tube.
5. Add 3 microliters of the First Strand Master Mix to each tube.
6. Mix by pipetting 5 times, spin and place on ice.
7. Place the tubes in a pre-cooled thermal cycler programmed as follow: 4 degrees Celsius—1 min, 25 degrees Celsius—10 min, 42 degrees Celsius—10 min, 70 degrees Celsius—15 min, hold at 4 degrees Celsius.
8. Remove the tubes and spin to collect condensation and place on ice.

Step-2: Second Strand cDNA Synthesis
1. Make a master mix by combining 9.7 microliters of B1 (Second Strand Buffer Mix) and 0.3 microliters of B2 (Second Strand Enzyme Mix) in a 0.5 ml capped tube.
2. Add 10 microliters of the Second Strand Master Mix to each First Strand reaction tube.
3. Mix by pipetting 5 times, spin and place on ice.
4. Place the tubes in a pre-cooled thermal cycler programmed as follow:
    4 degrees Celsius—1 min, 25 degrees Celsius—10 min, 50 degrees Celsius—30 min, 80 degrees Celsius—20 min, hold at 4 degrees Celsius.
5. Remove the tubes and spin to collect condensation and place on ice.

Step-3: Double-Strand cDNA was Purified with 1.4 Volumes of the Agencourt RNAClean XP Beads.

Step-4: Purified cDNA were Amplified with Single Primer Isothermal Amplification (SPIA).
1. Make a master mix by sequentially combining 20 microliters of C2 (SPIA Buffer Mix), 10 microliters of Cl (SPIA Primer Mix), 10 microliters of C3 (SPIA Enzyme Mix) in a capped tube.
2. Add 40 microliters of the SPIA Master Mix to each tube containing the double-strand cDNA bound to the dried beads. Use a pipette set to 30 microliters and mix thoroughly at least 8-10 times.
3. Place the tubes in a pre-cooled thermal cycler programmed as follow: 4 degrees Celsius—1 min, 47 degrees Celsius—120 min, 80 degrees Celsius—20 min, hold at 4 degrees Celsius.
4. Remove the tube from thermal cycler, spin to collect condensation and place on ice.
5. Transfer the tubes to the magnet and let stand for 5 min to completely clear the solution of beads.
6. Carefully transfer 40 microliters of the cleared supernatant containing the SPIA cDNA to a fresh tube.

Step-5: SPIA Amplified cDNA were Amplified with 0.8 Volumes of AMPure XP Beads.

Possible Variations
1. Step-1, more or less RNA samples could be used for the amplification step.
2. Step-3, the volumes of the Agencourt RNAClean XP beads can vary for different downstream applications.
3. Step-4, SPIA amplification step can vary for 60, 120, 180 min with different applications.
4. Step-5, the volumes of AMPure XP beads can vary for different downstream applications.

NGS Library Preparation—DNA

DNA library was conducted with KAPA HyperPlus Kits (KAPA Biosystem, Wilmington, Wash.) according to the modified manufacturer's instructions. Detailed protocol is as follows:
1. Enzymatic Fragmentation
    1. Dilute 500 ng input DNA with 10 mM Tris-HCl (pH8.0-8.5) in a total of 35 microliters.
    2. Assemble each fragmentation reaction on ice by adding the rest of the components in the order shown below:

| Component | Volume |
| --- | --- |
| dsDNA | 35 microliters |
| KAPAFrag Buffer (10x) | 5 microliters |
| KAPAFrag Enzyme | 10 microliters |
| Total Volume | 50 microliters |

3. Vortex gently and spin down briefly. Return the tubes to ice. Proceed immediately to the next step.
4. Incubate in a thermocycler, pre-cooled to 4 degrees Celsius and programmed as below. Set the lid temperature to ≤50 degrees Celsius.

| Step | Temp | Time |
| --- | --- | --- |
| Pre-cool block | 4 degrees Celsius | ∞ |
| Fragmentation | 37 degrees Celsius | 8 min |
| HOLD | 4 degrees Celsius | ∞ |

5. Transfer reactions to ice and proceed immediately to the next step.

2. End Repair and A-Tailing
1. In the same tubes, assemble each end repair and A-tailing reaction as follows:

| Component | Volume |
| --- | --- |
| Fragmented, dsDNA | 50 microliters |
| End Repair & A-tailing Buffer | 7 microliters |
| End Repair & A-tailing Enzyme Mix | 3 microliters |
| Total Volume | 60 microliters |

2. Vortex gently and spin down briefly.
3. Incubate the tubes at 65 degrees Celsius for 30 min and hold at 4 degrees Celsius. Set the lid temperature to 85 degrees Celsius.

3. Adapter Ligation
1. In the same tubes, assemble each adapter ligation reaction as follows:

| Component | Volume |
| --- | --- |
| End Repair & A-tailing reaction product | 60 microliters |
| Adapter stock 15 uM | 5 microliters |
| PCR grade water | 5 microliters |
| Ligation Buffer | 30 microliters |
| DNA ligase | 10 microliters |
| Total Volume | 110 microliters |

2. Mix thoroughly and centrifuge briefly, and incubate at 20 degrees Celsius for 30 min.

4. Post-Ligation Cleanup
1. In the same tubes, perform a 0.8×SPRI cleanup by combining the following:

| Component | Volume |
| --- | --- |
| Adapter ligation reaction product | 110 microliters |
| Agecourt AMPure XP reagent | 88 microliters |
| Total Volume | 198 microliters |

2. Mix thoroughly by pipetting up and down 10 times.
3. Incubate at room temperature for 10 min to bind DNA to the beads.
4. Place the tubes on a magnet to capture the beads. Incubate for about 5 min till the liquid is clear.
5. Carefully remove and discard the supernatant. Keep the tubes on the magnet and add 200 ul of 80% ethanol. Incubate the tubes at RT for ≥30 sec and remove the ethanol.
6. Repeat Step 5. Try to remove all residual ethanol without disturbing the beads.
7. Dry the beads at RT for 5 min. Remove the tubes from magnet and resuspend the beads in 55 microliters 10 mM Tris-HCl elution buffer.
8. Incubate the tubes at RT for 2 min to elute DNA off the beads.
9. Place the tubes on a magnet to capture the beads and incubate until the liquid is clear. Transfer 50 microliters cleared supernatant to new tubes.

5. Double-Size Selection
1. Perform the first 0.6× size cut to the tubes by adding 30 microliters AMPure XP reagent to eluted 50 microliters DNA library.
2. Mix thoroughly by pipetting up and down 10 times.
3. Incubate at room temperature for 10 min to bind library molecules larger than ~450 bp to the beads.
4. Place the tubes on a magnet to capture the beads. Incubate for about 5 min till the liquid is clear.
5. Transfer 75 microliters of supernatant containing library molecules smaller than ~450 bp to new tubes. No beads should be transferred with the supernatant.
6. Perform the second 0.7× size cut to the tubes by adding 5 microliters AMPure XP reagent.
7. Mix thoroughly by pipetting up and down 10 times.
8. Incubate at room temperature for 10 min to bind library molecules larger than ~300 bp to the beads.
9. Place the tubes on a magnet to capture the beads and incubate till the liquid is clear.
10. Remove and discard the supernatant, which contains library molecules smaller than ~300 bp. Keep the tubes on the magnet and add 200 microliters of 80% ethanol. Incubate the tubes at RT for ≥30 sec and remove the ethanol.
11. Repeat Step 5. Try to remove all residual ethanol without disturbing the beads.
12. Dry the beads at RT for 5 min. Remove the tubes from magnet and resuspend the beads in 25 microliters 10 mM Tris-HCl elution buffer.
13. Incubate the tubes at RT for 2 min to elute DNA off the beads.
14. Place the tubes on a magnet to capture the beads and incubate until the liquid is clear. Transfer 20 microliters cleared supernatant to new tubes for PCR amplification.

6. Library Amplification
1. Assemble each library amplification reaction as follows:

| Component | Volume |
| --- | --- |
| 2X KAPA HiFi HotStart ReadyMix | 25 microliters |
| 10X KAPA library amplification primer mix | 5 microliters |
| Adapter ligated library | 20 microliters |
| Total Volume | 50 microliters |

2. Mix thoroughly and centrifuge briefly.
3. Amplify using the cycling protocol as follows:

| Step | Temp | Duration | Cycles |
|---|---|---|---|
| Initial denaturation | 98 degrees Celsius | 45 sec | 1 |
| Denaturation | 98 degrees Celsius | 15 sec | |
| Annealing | 60 degrees Celsius | 30 sec | 3-4 |
| Extension | 72 degrees Celsius | 30 sec | |
| Final extension | 72 degrees Celsius | 1 min | 1 |
| HOLD | 4 degrees Celsius | ∞ | 1 |

7. Post-Amplification Cleanup
1. In each library amplification tube, perform a 0.7×SPRI cleanup by combining the following:

| Component | Volume |
|---|---|
| Library Amplification reaction product | 50 microliters |
| Agecourt AMPure XP reagent | 35 microliters |
| Total Volume | 85 microliters |

2. Mix thoroughly by pipetting up and down 10 times.
3. Incubate at room temperature for 10 min to bind DNA to the beads.
4. Place the tubes on a magnet to capture the beads. Incubate for about 5 min till the liquid is clear.
5. Carefully remove and discard the supernatant. Keep the tubes on the magnet and add 200 ul of 80% ethanol. Incubate the tubes at RT for ≥30 sec and remove the ethanol.
6. Repeat Step 5. Try to remove all residual ethanol without disturbing the beads.
7. Dry the beads at RT for 5 min. Remove the tubes from magnet and resuspend the beads in 35 microliters 10 mM Tris-HCl elution buffer.
8. Incubate the tubes at RT for 2 min to elute DNA off the beads.
9. Place the tubes on a magnet to capture the beads and incubate until the liquid is clear. Transfer 30 microliters cleared supernatant to new tubes.
10. HS Qubit will be used for the quantification of DNA library. Analysis of DNA fragments will be achieved by the Agilent 2100 Bioanalyzer.
11. 4 libraries with equal molarity are pooled and sequenced on NGS platform.

NGS Library Preparation—RNA cDNA library was conducted with KAPA HyperPlus Kits (KAPA Biosystem, Wilmington, Wash.) according to the modified manufacturer's instructions. Detailed protocol is as follows:

1. Enzymatic Fragmentation
1. Dilute 1-1000 ng input cDNA with 10 mM Tris-HCl (pH8.0-8.5) in a total of 35 microliters.
2. Assemble each fragmentation reaction on ice by adding the rest of the components in the order shown below:

| Component | Volume |
|---|---|
| dsDNA | 35 microliters |
| KAPA Frag Buffer (10x) | 5 microliters |
| KAPA Frag Enzyme | 10 microliters |
| Total Volume | 50 microliters |

3. Vortex gently and spin down briefly. Return the tubes to ice. Proceed immediately to the next step.
4. Incubate in a thermocycler, pre-cooled to 4® C. and programmed as below. Set the lid temperature to ≤50® C.

| Step | Temp | Time |
|---|---|---|
| Pre-cool block | 4 degrees Celsius | ∞ |
| Fragmentation | 25 degrees Celsius | 5 min |
| HOLD | 4 degrees Celsius | ∞ |

5. Transfer reactions to ice and proceed immediately to the next step.
3. End Repair and A-Tailing
4. In the same tubes, assemble each end repair and A-tailing reaction as follows:

| Component | Volume |
|---|---|
| Fragmented, dsDNA | 50 microliters |
| End Repair & A-tailing Buffer | 7 microliters |
| End Repair & A-tailing Enzyme Mix | 3 microliters |
| Total Volume | 60 microliters |

5. Vortex gently and spin down briefly.
6. Incubate the tubes at 65 degrees Celsius for 30 min and hold at 4 degrees Celsius. Set the lid temperature to 85 degrees Celsius.
3. Adapter Ligation
1. In the same tubes, assemble each adapter ligation reaction as follows:

| Component | Volume |
|---|---|
| End Repair & A-tailing reaction product | 60 microliters |
| Adapter stock 15uM | 5 microliters |
| PCR grade water | 5 microliters |
| Ligation Buffer | 30 microliters |
| DNA ligase | 10 microliters |
| Total Volume | 110 microliters |

2. Mix thoroughly and centrifuge briefly, and incubate at 20 degrees Celsius for 30 min.
4. Post-Ligation Cleanup
1. In the same tubes, perform a 0.8×SPRI cleanup by combining the following:

| Component | Volume |
|---|---|
| Adapter ligation reaction product | 110 microliters |
| Agencourt AMPure XP reagent | 88 microliters |
| Total Volume | 198 microliters |

2. Mix thoroughly by pipetting up and down 10 times.
3. Incubate at room temperature for 10 min to bind DNA to the beads.
4. Place the tubes on a magnet to capture the beads. Incubate for about 5 min till the liquid is clear.
5. Carefully remove and discard the supernatant. Keep the tubes on the magnet and add 200 microliters of 80% ethanol. Incubate the tubes at RT for ≥30 sec and remove the ethanol.

6. Repeat Step 5. Try to remove all residual ethanol without disturbing the beads.
7. Dry the beads at RT for 5 min. Remove the tubes from magnet and resuspend the beads in 23 microliters 10 mM Tris-HCl elution buffer.
8. Incubate the tubes at RT for 2 min to elute DNA off the beads.
9. Place the tubes on a magnet to capture the beads and incubate until the liquid is clear. Transfer 20 microliters cleared supernatant to new tubes.

5. Library Amplification
1. Assemble each library amplification reaction as follows:

| Component | Volume |
| --- | --- |
| 2X KAPA HiFi HotStart ReadyMix | 25 microliters |
| 10X KAPA library amplification primer mix | 5 microliters |
| Adapter ligated library | 20 microliters |
| Total Volume | 50 microliters |

2. Mix thoroughly and centrifuge briefly.
3. Amplify using the cycling protocol as follows:

| Step | Temp | Duration | Cycles |
| --- | --- | --- | --- |
| Initial denaturation | 98 degrees Celsius | 45 sec | 1 |
| Denaturation | 98 degrees Celsius | 15 sec | |
| Annealing | 60 degrees Celsius | 30 sec | 5-9 |
| Extension | 72 degrees Celsius | 30 sec | |
| Final extension | 72 degrees Celsius | 1 min | 1 |
| HOLD | 4 degrees Celsius | ∞ | 1 |

6. Post-Amplification Cleanup
1. In each library amplification tube, perform SPRI cleanup twice by combining the following:

| Component | First cleanup | Second cleanup |
| --- | --- | --- |
| Library Amplification reaction product | 50 mircoliters | 50 mircoliters |
| Agecourt AMPure XP reagent | 40 mircoliters | 35 mircoliters |
| Total Volume | 90 mircoliters | 85 mircoliters |

2. Mix thoroughly by pipetting up and down 10 times.
3. Incubate at room temperature for 10 min to bind DNA to the beads.
4. Place the tubes on a magnet to capture the beads. Incubate for about 5 min till the liquid is clear.
5. Carefully remove and discard the supernatant. Keep the tubes on the magnet and add 200 ul of 80% ethanol. Incubate the tubes at RT for ≥30 sec and remove the ethanol.
6. Repeat Step 5. Try to remove all residual ethanol without disturbing the beads.
7. Dry the beads at RT for 5 min. Remove the tubes from magnet and resuspend the beads in 53 microliters 10 mM Tris-HCl elution buffer.
8. Incubate the tubes at RT for 2 min to elute DNA off the beads.
9. Place the tubes on a magnet to capture the beads and incubate until the liquid is clear. Transfer 50 microliters cleared supernatant to new tubes.
10. Repeat steps 1-9 with second cleanup. In second cleanup, resuspend beads with 23 microliters 10 mM Tris-HCl elution buffer (step 7) and Transfer 20 microliters cleared supernatant to new tubes (step 9).
11. HS Qubit will be used for the quantification of DNA library. Analysis of DNA fragments will be achieved by the Agilent 2100 Bioanalyzer.
12. 4 libraries with equal molarity are pooled and sequenced on NGS platform.

What is claimed is:

1. An integrated collector device of environmental exposure for biotic and abiotic agents, comprising:
   (a) a housing with a front-end for air inlet and a rear-end for air outlet; and
   (b) an air pump situated within the housing and in between the air inlet and the air outlet, wherein the air pump is controlled to provide a constant air flow for air intake at the air inlet;
   (c) a membrane filter situated within the housing and in between the air flow from the front-end for air inlet and the air pump, wherein the membrane filter has pores with a pore size ranging from 0.1 to 5 μm to collect biotic agents from the constant air flow; and
   (d) a compound sorbent cartridge situated within the housing and in between the air flow from the air pump and the rear-end for air outlet, wherein the compound sorbent cartridge comprises compound adsorption resin beads and has pores ranging from 0.1 to 10 nm and a mesh size ranging from 45-60 mesh to collect abiotic agents.

2. The collector device as set forth in claim 1, wherein the membrane filter is a polyethersulfone (PES) membrane filter.

3. The collector device as set forth in claim 1, wherein the membrane filter is a regenerated cellulose membrane filter.

4. The collector device as set forth in claim 1, wherein the membrane filter has pores with a pore size ranging from 0.22 to 0.8 μm.

5. The collector device as set forth in claim 1, wherein compound sorbent cartridge comprises zeolite, graphene, or a combination thereof.

* * * * *